United States Patent [19]

Toda et al.

[11] Patent Number: 4,533,688

[45] Date of Patent: Aug. 6, 1985

[54] TRIS(PIPERIDYLAMINOTRIAZYLAMINO) COMPOUNDS, THEIR PREPARATION AND THEIR USE AS POLYMER STABILIZERS

[75] Inventors: Toshimasa Toda; Tomoyuki Kurumada, both of Hiromachi, Japan

[73] Assignee: Sankyo Company Limited, Tokyo, Japan

[21] Appl. No.: 562,707

[22] Filed: Dec. 19, 1983

[30] Foreign Application Priority Data

Dec. 28, 1982 [JP] Japan ................ 57-231356

[51] Int. Cl.$^3$ .................................................. C08K 5/34
[52] U.S. Cl. ...................................... 524/100; 544/198
[58] Field of Search .................... 524/100; 544/198

[56] References Cited

U.S. PATENT DOCUMENTS 4,263,434  4/1981  Cassandrini et al. ............. 524/100
4,321,374  3/1982  Morimura et al. ................ 524/100

Primary Examiner—John Kight
Assistant Examiner—Kriellion Morgan
Attorney, Agent, or Firm—Toren, McGeady, Stanger, Goldberg & Kiel

[57] ABSTRACT

Bis(piperidylaminotriazylamino)-(piperidylaminotriazylaminomethyl)-octane derivatives are novel compounds which are valuable as stabilizers for synthetic polymers.

28 Claims, No Drawings

TRIS(PIPERIDYLAMINOTRIAZYLAMINO) COMPOUNDS, THEIR PREPARATION AND THEIR USE AS POLYMER STABILIZERS

BACKGROUND TO THE INVENTION

The present invention relates to a series of new tris(-piperidylaminotriazylamino) compounds and to their use as stabilizers for synthetic polymers.

In recent years, a number of triazine derivatives have been proposed for use as polymer stabilizers, for example, as disclosed in U.S. Pat. Nos. 4,108,829, 4,234,728 and 4,321,374. However, although the prior art compounds are, in general, effective stabilizers for synthetic polymers, particularly against light-induced degradation of polyolefins, they have a number of disadvantages in certain applications. In particular, these compounds have a relatively high volatility and tendency to migrate; moreover, their compatibility with polymers is generally not wholly satisfactory. Because of these problems, they tend to migrate easily to the surfaces of articles manufactured from the polymers which they are intended to stabilize, resulting in blooming and, in the long term, a reduction in the stabilization. This is particularly the case when the polymeric material is used in thin articles, such as in fibres, films or lacquers, and stabilization of polymeric articles of this type over a long period becomes an important problem.

We have now surprisingly discovered a series of triazine derivatives which can be dissolved in the polymers to be protected (thus overcoming the disadvantages of incompatibility which occur with simple physical mixtures), which have a low volatility and tendency to migrate and which are excellent light stabilizers for polymeric materials.

BRIEF SUMMARY OF THE INVENTION

The compounds of the present invention are tris(-piperidylaminotriazylamino) compounds of formula (I):

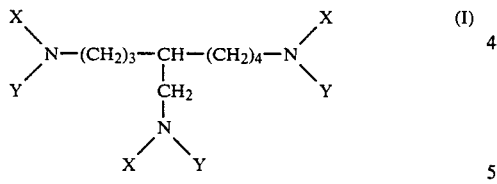

in which: the groups represented by X are the same and have the formula (II):

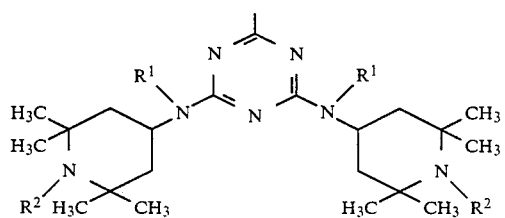

(in which:

$R^1$ represents a hydrogen atom, a $C_1$–$C_{18}$ alkyl group, a $C_2$–$C_{22}$ alkoxyalkyl group, a $C_1$–$C_{18}$ acyl group, an aralkyl group optionally having at least one $C_1$–$C_4$ alkyl or halogen substituent or a group of formula (III):

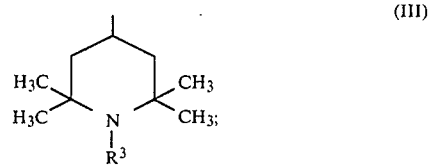

and $R^2$ and $R^3$ are the same or different and each represents a hydrogen atom, a $C_1$–$C_{18}$ alkyl group, a $C_1$–$C_{18}$ acyl group or an aralkyl group optionally having at least one $C_1$–$C_4$ alkyl or halogen substituent); and Y represents a hydrogen atom, a $C_1$–$C_{18}$ alkyl group, a $C_1$–$C_{18}$ acyl group, an aralkyl group optionally having at least one $C_1$–$C_4$ alkyl or halogen substituent or a group of formula (IV):

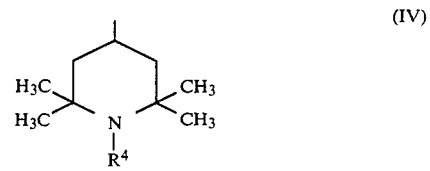

in which $R^4$ has any of the meanings defined for $R^2$; and acid addition salts thereof.

The invention further provides a synthetic polymer composition comprising a synthetic polymer stabilised against the effects of light by the incorporation of a polymer stabilizer, wherein the stabilizer comprises at least one compound selected from compounds of formula (I) and their acid addition salts.

DETAILED DESCRIPTION OF INVENTION

In the compounds of formula (I), where $R^1$, $R^2$, $R^3$, $R^4$ or Y represents a $C_1$–$C_{18}$ alkyl group, this may be a straight or branched chain group, for example a methyl, ethyl, propyl, isopropyl, butyl, hexyl, octyl, 2-ethylhexyl, decyl, dodecyl or octadecyl group. In the case of $R^1$, the alkyl group preferably has from 4 to 8 carbon atoms, the butyl, hexyl, octyl and 2-ethylhexyl groups being most preferred. In the case of $R^2$, $R^3$, $R^4$ and Y, the group preferably has from 1 to 4 carbon atoms, the methyl, ethyl, propyl, isopropyl and butyl groups being preferred and the methyl group being most preferred.

Where $R^1$ represents an alkoxyalkyl group, it has from 2 to 22 carbon atoms, preferably from 3 to 22 carbon atoms, and we particularly prefer that the alkyl group should have from 2 to 4 carbon atoms, whilst the alkoxy group should have from 1 to 18 carbon atoms. This alkoxy group may be a straight or branched chain group, for example the methoxy, ethoxy, propoxy, isopropoxy, butoxy, hexyloxy, octyloxy, 2-ethylhexyloxy, decyloxy, dodecyloxy or octadecyloxy groups. The preferred alkoxy groups have from 1 to 8 carbon atoms, for example the methoxy, ethoxy, propoxy, isopropoxy, butoxy, heptyloxy or octyloxy groups. The alkyl group may be a straight or branched chain group and preferably has from 2 to 4 carbon atoms, for example an ethyl, propyl, isopropyl, butyl or isobutyl group, most preferably a propyl group.

When $R^1$, $R^2$, $R^3$, $R^4$ or Y represents an acyl group, this has from 1 to 18 carbon atoms, preferably from 2 to 18 carbon atoms, and is preferably an aliphatic carboxylic group (which can be saturated or unsaturated and straight or branched chain) or an aromatic carboxylic group, for example an acetyl, propionyl, acryloyl, butyroyl, hexanoyl, benzoyl, octanoyl, lauroyl, palmitoyl or stearoyl group. In particular, we prefer saturated straight-chain aliphatic carboxylic groups having from 2 to 4 carbon atoms, of which the acetyl group is most preferred.

Where $R^1$, $R^2$, $R^3$, $R^4$ or Y represents an optionally substituted aralkyl group, the substituents are chosen from $C_1$-$C_4$ alkyl groups and halogen atoms and there may be one or more, preferably one, substituent and, where there is more than one substituent, these may be the same or different. Examples of such optionally substituted aralkyl groups include the benzyl, phenethyl, p-methylbenzyl and p-chlorobenzyl groups, of which the benzyl group is preferred.

For ease of preparation, those compounds of formula (I) are preferred in which:

where $R^1$ and Y both represent acyl groups, these acyl groups are the same;

where one of $R^1$ and Y represents an acyl group, the other does not represent a hydrogen atom;

where two or three of $R^2$, $R^3$ and $R^4$ represent acyl groups, these acyl groups are the same; and where one or two of $R^2$, $R^3$ and $R^4$ represent acyl groups, the other or others do not represent hydrogen atoms.

Particularly preferred are compounds in which:

where two or more of $R^1$, $R^2$, $R^3$, $R^4$ and Y represent acyl groups, these acyl groups are the same; and where one or more of $R^1$, $R^2$, $R^3$, $R^4$ and Y represent acyl groups, the other or others do not represent hydrogen atoms.

Preferred classes of compound of the present invention are those in which:

(1) Y represents a hydrogen atom, a $C_1$-$C_{18}$ alkyl group, a $C_2$-$C_{18}$ acyl group or an aralkyl group optionally having a $C_1$-$C_4$ alkyl or halogen substituent, more preferably a hydrogen atom or a methyl or acetyl group;

(2) $R^2$ and $R^3$ are the same and each represents a hydrogen atom or a methyl or acetyl group and preferably Y is as defined in (1) above;

(3) Y and $R^2$, which may be the same or different, each represents a hydrogen atom or a methyl group, and $R^1$ represents a hydrogen atom, a $C_1$-$C_{18}$ alkyl group or a $C_3$-$C_{22}$ alkoxyalkyl group; and (4) Y and $R^2$, which may be the same or different, each represents a hydrogen atom or a methyl group, and $R^1$ represents a hydrogen atom or a $C_4$-$C_8$ alkyl group.

The tris(piperidylaminotriazylamino) compounds of the present invention form acid addition salts, which are also part of the present invention. The nature of these salts is not critical, provided that they do not or do not substantially detract from the stabilizing effect of the compound of formula (I). Examples of acids which can usefully form salts with the compounds of formula (I) include: inorganic acids, such as sulphuric acid, hydrochloric acid or phosphoric acid; organic carboxylic acids, such as formic acid, acetic acid, valeric acid, stearic acid, oxalic acid, adipic acid, sebacic acid, maleic acid, benzoic acid, p-t-butylbenzoic acid, 3,5-di-t-butyl-4-hydroxybenzoic acid, salicyclic acid or terephthalic acid; organic sulphonic acids, such as methanesulphonic acid, benzenesulphonic acid or p-toluenesulphonic acid; or organic phosphonic acids, such as phenylphosphonic acid.

Examples of the tris(piperidylaminotriazylamino) compounds of the present invention are given in the following list. Where appropriate, the compounds of the invention are hereinafter identified by the numbers appended to them in this list:

1. 1,8-Bis(N-[2,4-bis(2,2,6,6-tetramethylpiperid-4-ylamino)-1,3,5-triazin-6-yl]amino)-4-(N-[2,4-bis(2,2,6,6-tetramethylpiperid-4-ylamino)-1,3,5-triazin-6-yl]aminomethyl)octane 2. 1,8-Bis(N-[2,4-bis(1,2,2,6,6-pentamethylpiperid-4-ylamino)-1,3,5-triazin-6-yl]amino)-4-(N-[2,4-bis(1,2,2,6,6-pentamethylpiperid-4-ylamino)-1,3,5-triazin-6-yl]aminomethyl)octane 3. 1,8-Bis[N-(2,4-bis[N-methyl-N-(2,2,6,6-tetramethylpiperid-4-yl)amino]-1,3,5-triazin-6-yl)amino]-4-[N-(2,4-bis[N-methyl-N-(2,2,6,6-tetramethylpiperid-4-yl)amino]-1,3,5-triazin-6-yl)aminomethyl]octane 4. 1,8-Bis[N-methyl-N-(2,4-bis[N-methyl-N-(1,2,2,6,6-pentamethylpiperid-4-yl)amino]-1,3,5-triazin-6-yl)amino]-4-[N-methyl-N-(2,4-bis[N-methyl-N-(1,2,2,6,6-pentamethylpiperid-4-yl)amino]-1,3,5-triazin-6-yl)aminomethyl]octane 5. 1,8-Bis[N-(2,4-bis[N-ethyl-N-(2,2,6,6-tetramethylpiperid-4-yl)amino]-1,3,5-triazin-6-yl)amino]-4-[N-(2,4-bis[N-ethyl-N-(2,2,6,6-tetramethylpiperid-4-yl)amino]-1,3,5-triazin-6-yl)aminomethyl]octane 6. 1,8-Bis[N-(2,4-bis[N-propyl-N-(2,2,6,6-tetramethylpiperid-4-yl)amino]-1,3,5-triazin-6-yl)amino]-4-[N-(2,4-bis[N-propyl-N-(2,2,6,6-tetramethylpiperid-4-yl)amino]-1,3,5-triazin-6-yl)aminomethyl]octane 7. 1,8-Bis[N-(2,4-bis[N-butyl-N-(2,2,6,6-tetramethylpiperid-4-yl)amino]-1,3,5-triazin-6-yl)amino]-4-[N-(2,4-bis[N-butyl-N-(2,2,6,6-tetramethylpiperid-4-yl)amino]-1,3,5-triazin-6-yl)aminomethyl]octane 8. 1,8-Bis[N-methyl-N-(2,4-bis[N-butyl-N-(1,2,2,6,6-pentamethylpiperid-4-yl)amino]-1,3,5-triazin-6-yl)amino]-4-[N-methyl-N-(2,4-bis[N-butyl-N-(1,2,2,6,6-pentamethylpiperid-4-yl)amino]-1,3,5-triazin-6-yl)aminomethyl]octane 9. 1,8-Bis[N-acetyl-N-(2,4-bis[N-butyl-N-(1-acetyl-2,2,6,6-tetramethylpiperid-4-yl)amino]-1,3,5-triazin-6-yl)amino]-4-[N-acetyl-N-(2,4-bis[N-butyl-N-(1-acetyl-2,2,6,6-tetramethylpiperid-4-yl)amino]-1,3,5-triazin-6-yl)aminomethyl]octane 10. 1,8-Bis[N-benzyl-N-(2,4-bis[N-butyl-N-(1-benzyl-2,2,6,6-tetramethylpiperid-4-yl)amino]-1,3,5-triazin-6-yl)amino]-4-[N-benzyl-N-(2,4-bis[N-butyl-N-(1-benzyl-2,2,6,6-tetramethylpiperid-4-yl)amino]-1,3,5-triazin-6-yl)aminomethyl]octane 11. 1,8-Bis[N-(2,2,6,6-tetramethylpiperid-4-yl)-N-(2,4-bis[N-butyl-N-(2,2,6,6-tetramethylpiperid-4-yl)amino]-1,3,5-triazin-6-yl)amino]-4-[N-(2,2,6,6-tetramethylpiperid-4-yl)-N-(2,4-bis[N-butyl-N-(2,2,6,6-tetramethylpiperid-4-yl)amino]-1,3,5-triazin-6-yl)aminomethyl]octane 12. 1,8-Bis[N-(2,4-bis[N-isobutyl-N-(2,2,6,6-tetramethylpiperid-4-yl)amino]-1,3,5-triazin-6-yl)amino]-4-[N-(2,4-bis[N-isobutyl-N-(2,2,6,6-tetramethylpiperid-4-yl)amino]-1,3,5-triazin-6-yl)aminomethyl]octane 13. 1,8-Bis[N-(2,4-bis[N-hexyl-N-(2,2,6,6-tetramethylpiperid-4-yl)amino]-1,3,5-triazin-6-yl)amino]-4-[N-(2,4-bis[N-hexyl-N-(2,2,6,6-tetramethylpiperid-4-yl)amino]-1,3,5-triazin-6-yl)aminomethyl]octane 14. 1,8-Bis[N-(2,4-bis[N-octyl-N-(2,2,6,6-tetramethylpiperid-4-yl)amino]-1,3,5-triazin-6-yl)amino]-4-[N-

(2,4-bis[N-octyl-N-(2,2,6,6-tetramethylpiperid-4-yl)amino]-1,3,5-triazin-6-yl)aminomethyl]octane 15. 1,8-Bis[N-methyl-N-(2,4-bis[N-octyl-N-(1,2,2,6,6-pentamethylpiperid-4-yl)amino]-1,3,5-triazin-6-yl)amino]-4-[N-methyl-N-(2,4-bis[N-octyl-N-(1,2,2,6,6-pentamethylpiperid-4-yl)amino]-1,3,5-triazin-6-yl)aminomethyl]octane 16. 1,8-Bis[N-acetyl-N-(2,4-bis[N-octyl-N-(1-acetyl-2,2,6,6-tetramethylpiperid-4-yl)amino]-1,3,5-triazin-6-yl)amino]-4-[N-acetyl-N-(2,4-bis[N-octyl-N-(1-acetyl-2,2,6,6-tetramethylpiperid-4-yl)amino]-1,3,5-triazin-6-yl)aminomethyl]octane 17. 1,8-Bis[N-(2,2,6,6-tetramethylpiperid-4-yl)-N-(2,4-bis[N-octyl-N-(2,2,6,6-tetramethylpiperid-4-yl)amino]-1,3,5-triazin-6-yl)amino]-4-[N-(2,2,6,6-tetramethylpiperid-4-yl)-N-(2,4-bis[N-octyl-N-(2,2,6,6-tetramethylpiperid-4-yl)amino]-1,3,5-triazin-6-yl)aminomethyl]octane 18. 1,8-Bis[N-(2,4-bis[N-(2-ethylhexyl)-N-(2,2,6,6-tetramethylpiperid-4-yl)amino]-1,3,5-triazin-6-yl)amino]-4-[N-(2,4-bis[N-(2-ethylhexyl)-N-(2,2,6,6-tetramethylpiperid-4-yl)amino]-1,3,5-triazin-6-yl)aminomethyl]octane 19. 1,8-Bis[N-(1,2,2,6,6-pentamethylpiperid-4-yl)-N-(2,4-bis[N-(2-ethylhexyl)-N-(1,2,2,6,6-pentamethylpiperid-4-yl)amino]-1,3,5-triazin-6-yl)amino]-4-[N-(1,2,2,6,6-pentamethylpiperid-4-yl)-N-(2,4-bis[N-(2-ethylhexyl)-N-(1,2,2,6,6-pentamethylpiperid-4-yl)amino]-1,3,5-triazin-6-yl)aminomethyl]octane 20. 1,8-Bis[N-acetyl-N-(2,4-bis[N-(2-ethylhexyl)-N-(1-acetyl-2,2,6,6-tetramethylpiperid-4-yl)amino]-1,3,5-triazin-6-yl)amino]-4-[N-acetyl-N-(2,4-bis[N-(2-ethylhexyl)-N-(1-acetyl-2,2,6,6-tetramethylpiperid-4-yl)amino]-1,3,5-triazin-6-yl)aminomethyl]octane 21. 1,8-Bis[N-(2,4-bis[N-dodecyl-N-(2,2,6,6-tetramethylpiperid-4-yl)amino]-1,3,5-triazin-6-yl)amino]-4-[N-(2,4-bis[N-dodecyl-N-(2,2,6,6-tetramethylpiperid-4-yl)amino]-1,3,5-triazin-6-yl)aminomethyl]octane 22. 1,8-Bis[N-benzyl-N-(2,4-bis[N-dodecyl-N-(1-benzyl-2,2,6,6-tetramethylpiperid-4-yl)amino]-1,3,5-triazin-6-yl)amino]-4-[N-benzyl-N-(2,4-bis[N-dodecyl-N-(1-benzyl-2,2,6,6-tetramethylpiperid-4-yl)amino]-1,3,5-triazin-6-yl)aminomethyl]octane 23. 1,8-Bis[N-acetyl-N-(2,4-bis[N-dodecyl-N-(1-acetyl-2,2,6,6-tetramethypiperid-4-yl)amino]-1,3,5-triazin-6-yl)amino]-4-[N-acetyl-N-(2,4-bis[N-dodecyl-N-(1-acetyl-2,2,6,6-tetramethylpiperid-4-yl)amino]-1,3,5-triazin-6-yl)aminomethyl]octane 24. 1,8-Bis[N-(2,4-bis[N-octadecyl-N-(2,2,6,6-tetramethylpiperid-4-yl)amino]-1,3,5-triazin-6-yl)amino]-4-[N-(2,4-bis[N-octadecyl-N-(2,2,6,6-tetramethylpiperid-4-yl)amino]-1,3,5-triazin-6-yl)aminomethyl]octane 25. 1,8-Bis[N-methyl-N-(2,4-bis[N-octadecyl-N-(1,2,2,6,6-pentamethylpiperid-4-yl)amino]-1,3,5-triazin-6-yl)amino]-4-[N-methyl-N-(2,4-bis[N-octadecyl-N-(1,2,2,6,6-pentamethyl-piperid-4-yl)amino]-1,3,5-triazin-6-yl)aminomethyl]octane 26. 1,8-Bis[N-acetyl-N-(2,4-bis[N-octadecyl-N-(1-acetyl-2,2,6,6-tetramethylpiperid-4-yl)amino]-1,3,5-triazin-6-yl)amino]-4-[N-acetyl-N-(2,4-bis[N-octadecyl-N-(1-acetyl-2,2,6,6-tetramethylpiperid-4-yl)amino]-1,3,5-triazin-6-yl)aminomethyl]octane 27. 1,8-Bis[N-(2,4-bis[N-(2-methoxyethyl)-N-(2,2,6,6-tetramethylpiperid-4-yl)amino]-1,3,5-triazin-6-yl)amino]-4-[N-(2,4-bis[N-(2-methoxyethyl)-N-(2,2,6,6-tetramethylpiperid-4-yl)amino]-1,3,5-triazin-6-yl)aminomethyl]octane 28. 1,8-Bis[N-(2,4-bis[N-(2-ethoxyethyl)-N-(2,2,6,6-tetramethylpiperid-4-yl)amino]-1,3,5-triazin-6-yL)amino]-4-[N-(2,4-bis[N-(2-ethoxyethyl)-N-(2,2,6,6-tetramethylpiperid-4-yl)amino]-1,3,5-triazin-6-yl)aminomethyl]octane 29. 1,8-Bis[N-(2,4-bis[N-(2-propoxyethyl)-N-(1,2,2,6,6-pentamethylpiperid-4-yl)amino]-1,3,5-triazin-6-yl)amino]-4-[N-(2,4-bis[N-(2-propoxyethyl)-N-(1,2,2,6,6-pentamethylpiperid-4-yl)amino]-1,3,5-triazin-6-yl)aminomethyl]octane 30. 1,8-Bis[N-(2,4-bis[N-(2-methoxypropyl)-N-(2,2,6,6-tetramethylpiperid-4-yl)amino]-1,3,5-triazin-6-yl)amino]-4-[N-(2,4-bis[N-(2-methoxypropyl)-N-(2,2,6,6-tetramethylpiperid-4-yl)amino]-1,3,5-triazin-6-yl)aminomethyl]octane 31. 1,8-Bis[N-methyl-N-(2,4-bis[N-(2-ethoxy-1-methylethyl)-N-(2,2,6,6-tetramethylpiperid-4-yl)amino]-1,3,5-triazin-6-yl)amino]-4-[N-methyl-N-(2,4-bis[N-(2-ethoxy-1-methylethyl)-N-(2,2,6,6-tetramethylpiperid-4-yl)amino]-1,3,5-triazin-6-yl)aminomethyl]octane 32. 1,8-Bis[N-(3-methoxypropyl)-N-(2,2,6,6-tetramethylpiperid-4-yl)amino]-1,3,5-triazin-6-yl)amino]-4-[N-(2,4-bis[N-(3-methoxypropyl)-N-(2,2,6,6-tetramethylpiperid-4-yl)amino]-1,3,5-triazin-6-yl)aminomethyl]octane 33. 1,8-Bis[N-methyl-N-(2,4-bis[N-(3-methoxypropyl)-N-(1,2,2,6,6-pentamethylpiperid-4-yl)amino]-1,3,5-triazin-6-yl)amino]-4-[N-methyl-N-(2,4-bis[N-(3-methoxypropyl)-N-(1,2,2,6,6-pentamethylpiperid-4-yl)amino]-1,3,5-triazin-6-yl)aminomethyl]octane 34. 1,8-Bis[N-acetyl-N-(2,4-bis[N-(3-methoxypropyl)-N-(1-acetyl-2,2,6,6-tetramethylpiperid-4-yl)amino]-1,3,5-triazin-6-yl)amino]-4-[N-acetyl-N-(2,4-bis[N-(3-methoxypropyl)-N-(1-acetyl-2,2,6,6-tetramethylpiperid-4-yl)amino]-1,3,5-triazin-6-yl)aminomethyl]octane 35. 1,8-Bis[N-(2,4-bis[N-(3-ethoxypropyl)-N-(2,2,6,6-tetramethylpiperid-4-yl)amino]-1,3,5-triazin-6-yl)amino]-4-[N-(2,4-bis[N-(3-ethoxypropyl)-N-(2,2,6,6-tetramethylpiperid-4-yl)amino]-1,3,5-triazin-6-yl)aminomethyl]octane 36. 1,8-Bis[N-benzyl-N-(2,4-bis[N-(3-ethoxypropyl)-N-(1-benzyl-2,2,6,6-tetramethylpiperid-4-yl)amino]-1,3,5-triazin-6-yl)amino]-4-[N-benzyl-N-(2,4-bis[N-(3-ethoxypropyl)-N-(1-benzyl-2,2,6,6-tetramethylpiperid-4-yl)amino]-1,3,5-triazin-6-yl)aminomethyl]octane 37. 1,8-Bis[N-(2,4-bis[N-(3-butoxypropyl)-N-(2,2,6,6-tetramethylpiperid-4-yl)amino]-1,3,5-triazin-6-yl)amino]-4-[N-(2,4-bis[N-(3-butoxypropyl)-N-(2,2,6,6-tetramethylpiperid-4-yl)amino]-1,3,5-triazin-6-yl)aminomethyl]octane 38. 1,8-Bis[N-(2,4-bis[N-(3-2'-ethylhexyloxypropyl)-N-(2,2,6,6-tetramethylpiperid-4-yl)amino]-1,3,5-triazin-6-yl)amino]-4-[N-(2,4-bis[N-(3-2'-ethylhexyloxypropyl)-N-(2,2,6,6-tetramethylpiperid-4-yl)amino]-1,3,5-triazin-6-yl)aminomethyl]octane 39. 1,8-Bis[N-benzyl-N-(2,4-bis[N-benzyl-N-(1-benzyl-2,2,6,6-tetramethylpiperid-4-yl)amino]-1,3,5-triazin-6-yl)amino]-4-[N-benzyl-N-(2,4-bis[N-benzyl-N-(1-benzyl-2,2,6,6-tetramethylpiperid-4-yl)amino]-1,3,5-triazin-6-yl)aminomethyl]octane 40. 1,8-Bis[N-acetyl-N-(2,4-bis[N-acetyl-N-(1-acetyl-2,2,6,6-tetramethylpiperid-4-yl)amino]-1,3,5-triazin-6-yl)amino]-4-[N-acetyl-N-(2,4-bis[N-acetyl-N-(1-acetyl-2,2,6,6-tetramethylpiperid-4-yl)amino]-1,3,5-triazin-6-yl)aminomethyl]octane 41. 1,8-Bis[N-(2,4-bis[N,N-bis(2,2,6,6-tetramethylpiperid-4-yl)amino]-1,3,5-triazin-6-yl)amino]-4-[N-(2,4-bis[N,N-bis(2,2,6,6-tetramethylpiperid-4-yl)amino]-1,3,5-triazin-6-yl)aminomethyl]octane
42. 1,8-Bis[N-(2,2,6,6-tetramethylpiperid-4-yl)-N-(2,4-bis[N,N-bis(2,2,6,6-tetramethylpiperid-4-yl)amino]-1,3,5-triazin-6-yl)amino]-4-[N-(2,2,6,6-tetramethylpiperid-4-yl)-N-(2,4-bis[N,N-bis(2,2,6,6-tetramethylpiperid-4-yl)amino]-1,3,5-triazin-6-yl)aminomethyl]octane Of the compounds listed above, preferred compounds are Compounds Nos. 7, 8 and 14, of which Compound No. 7 is most preferred.

The compounds of formula (I) may be prepared by reacting a compound of formula (VIII):

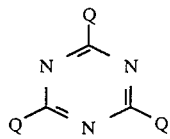
(VIII)

(in which Q represents a halogen atom, for example a chlorine, bromine or iodine atom, preferably a chlorine atom) with a compound of formula (VII):

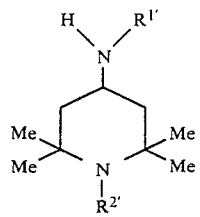
(VII)

and with a compound of formula (X):

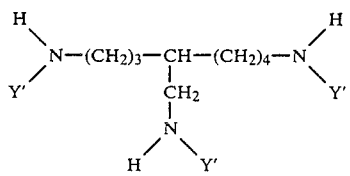
(X)

in any order, i.e. compound (VIII) is first reacted with compound (VII) and then the product is reacted with compound (X) or compound (VIII) is reacted with compound (X) and then the product is reacted with compound (VII).

In the above formulae:

$R^{1'}$ represents a hydrogen atom, a $C_1$–$C_{18}$ alkyl group, a $C_2$–$C_{22}$ (preferably $C_3$–$C_{22}$) alkoxyalkyl group, an aralkyl group optionally having at least one $C_1$–$C_4$ alkyl or halogen substituent, or a group of formula (IIIa):

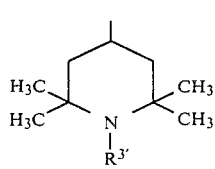
(IIIa)

i.e. $R^{1'}$ represents any of the definitions given for $R^1$, except an acyl group;

$Y'$ represents a hydrogen atom, a $C_1$–$C_{18}$ alkyl group, an aralkyl group optionally having at least one $C_1$–$C_4$ alkyl or halogen substituent, or a group of formula (IVa):

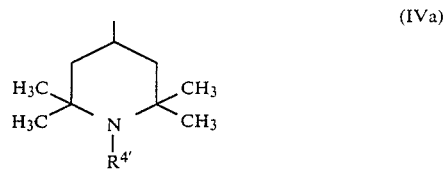
(IVa)

i.e. $Y'$ represents any of the definitions given for Y, except an acyl group; and $R^{2'}$, $R^{3'}$ and $R^{4'}$ are the same or different and each represents a hydrogen atom, a $C_1$–$C_{18}$ alkyl group or an aralkyl group optionally having at least one $C_1$–$C_4$ alkyl or halogen substituent, i.e. $R^{2'}$, $R^{3'}$ and $R^{4'}$ represent any of the definitions given for $R^2$, $R^3$ and $R^4$, respectively, except an acyl group.

If it is desired to prepare a compound in which any one or more of $R^1$, $R^2$, $R^3$, $R^4$ and Y represent acyl groups, then the corresponding compound in which $R^{1'}$, $R^{2'}$, $R^{3'}$, $R^{4'}$ or $Y'$ represents a hydrogen atom may be acylated.

The process of the invention is preferably carried out following either of the following Methods.

METHOD A

Compounds of formula (Ia) may be prepared as illustrated by the following reaction scheme:

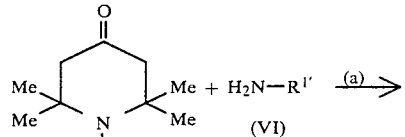
(V)

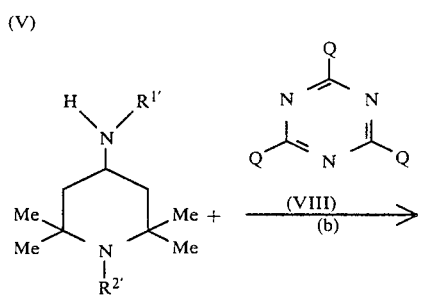
(VII)

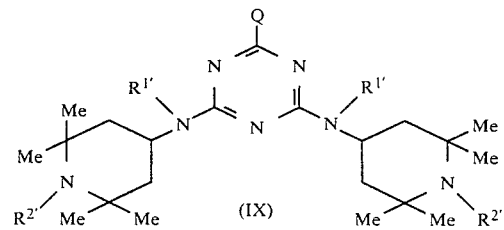
(IX)

-continued

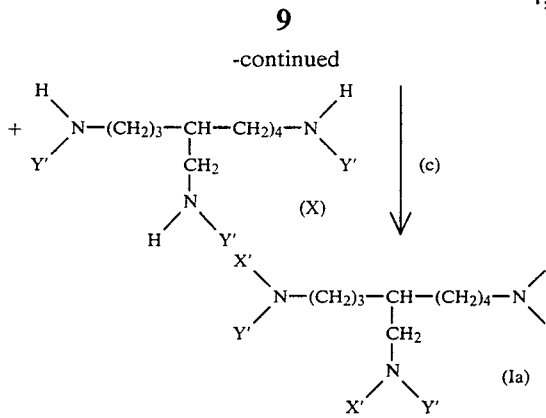

In the above reaction scheme, $R^{1'}$, $R^{2'}$, $Y'$ and Q are as defined above and $X'$ represents a group of formula (IIa):

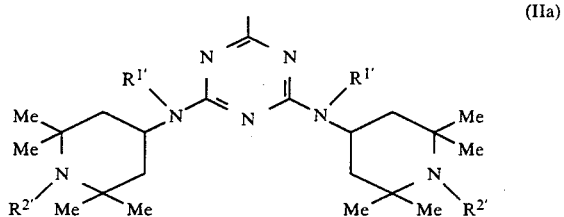

In formula (IIa) and in the reaction schemes, the methyl group has been abbreviated a "Me".

In step (a) of this reaction scheme, a compound of formula (V) is reacted with an amine of formula (VI) under catalytic hydrogenation conditions, to give a compound of formula (VII).

Any catalyst commonly used in catalytic hydrogenation reactions may be employed for this reaction, without any particular limitation. Preferred catalysts include palladium on activated carbon, palladium black, platinum oxide and Raney nickel, of which platinum oxide is particularly preferred.

The reaction is preferably effected in the presence of a solvent, the nature of which is not critical, provided that it has no adverse effect on the reaction. Suitable solvents include water, an alcohol (such as methanol, ethanol or propanol) or a mixture thereof.

The hydrogen pressure employed is generally from 1 to 10 atmospheres (from 1.01 to 10.13 bars). The reaction temperature may vary over a wide range but is preferably from ambient temperature to 100° C. The time required for the reaction will vary, depending upon the nature of the starting materials, the kind of catalyst employed and the reaction temperature, but, in general, a period of from 30 minutes to 5 hours will suffice.

The compound of formula (VI) can be employed in the form of its salt. Examples of salts which may be used include: salts of mineral acids, such as hydrochloric acid, nitric acid or sulphuric acid; salts of organic carboxylic acids, such as acetic acid, trifluoroacetic acid, adipic acid or benzoic acid; salts of organic sulphonic acids, such as methanesulphonic acid, benzenesulphonic acid or p-toluenesulphonic acid; and salts of organic phosphonic acids, such as phenylphosphonic acid.

Compounds of formula (VII) in which $R^{1'}$ represents a group of formula (IIIa) may be prepared directly by reacting a compound of formula (V) with an ammonium salt, such as ammonium chloride, ammonium bromide or ammonium acetate.

In step (b) of the reaction scheme, a compound of formula (IX) is prepared by reacting an appropriate amount of the compound of formula (VII) with a compound of formula (VIII) in an inert solvent.

The nature of the solvent employed in this reaction is not critical, provided that it has no adverse effect on the reaction. Suitable solvents include: water; ketones, such as acetone or methyl ethyl ketone; ethers, such as diethyl ether, tetrahydrofuran or dioxane; aromatic hydrocarbons, such as benzene, toluene or xylene; saturated hydrocarbons, such as heptane, octane, isooctane, cyclohexane or ethylcyclohexane; and mixtures of any two or more of the above solvents, mixtures of one or more of the above organic solvents with water being preferred and aqueous acetone being most preferred.

The temperature employed for this reaction may vary over a wide range, for example from 0° C. to 200° C., but we prefer to carry out the reaction at a temperature within the range from room temperature to 150° C. The time required for the reaction will vary, depending upon the nature of the starting materials and the reaction temperature but, in general, the reaction will require a period of from 30 minutes to 25 hours.

This reaction may be facilitated by the presence of an acid-acceptor, which may be, for example: an inorganic base, such as sodium hydroxide, potassium hydroxide, sodium carbonate or potassium carbonate; or an organic base, such as triethylamine, pyridine, N,N-dimethylaniline or 1,8-diazabicyclo[4.3.0]undec-7-ene. Of these, we prefer sodium hydroxide, potassium hydroxide, sodium carbonate or potassium carbonate.

In step (c) of this reaction scheme, a compound of formula (Ia) is prepared by reacting the compound of formula (IX) with a compound of formula (X) in an inert solvent. The reaction conditions employed may be as described for step (b), but the reaction temperature is preferably from 100° C. to 200° C. and the time required for the reaction will generally be from 5 hours to 25 hours.

The starting material of formula (X) in which $Y'$ represents an alkyl group, an aralkyl group or a group of formula (IVa) may easily be prepared by reacting the corresponding compound of formula (X) in which $Y'$ represents a hydrogen atom with the corresponding carbonyl derivative, employing the reductive amination reaction described in step (a).

METHOD B

In this Method, a compound of formula (Ia) is prepared using similar reactions to those in Method A, but changing the order of the reactions. The first step in Method B, step (a'), consists of reacting a compound of formula (VIII) with a compound of formula (X) under the same reaction conditions as are employed in step (b) of Method A.

The second step, step (b'), of Method B comprises reacting the resulting compound of formula (XI) with a compound of formula (VII), following the same procedure as described for step (c) of Method A, resulting in the desired compound of formula (Ia).

These steps are shown in the following reaction scheme:

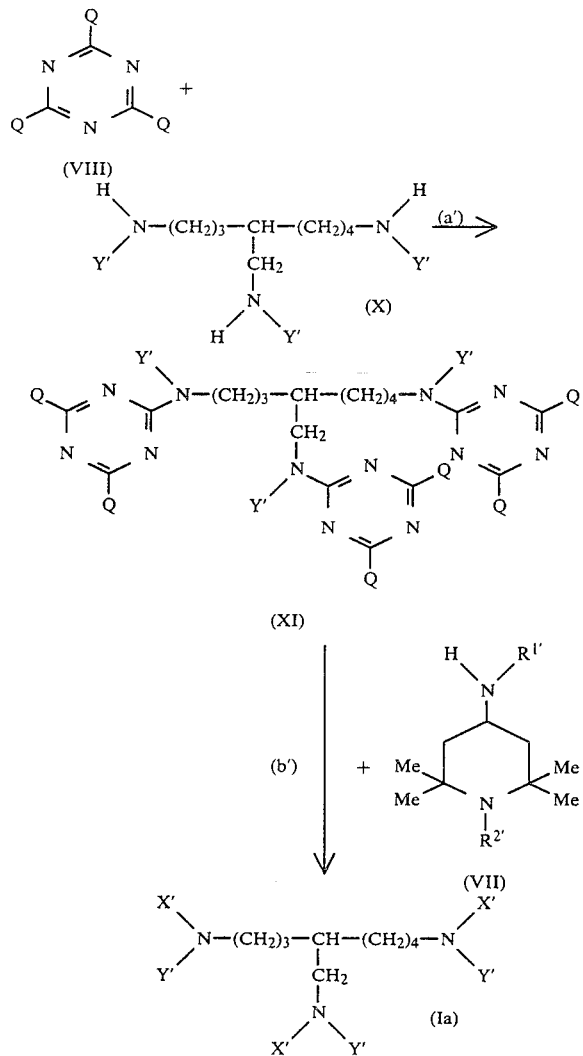

If desired, the resulting compounds of formula (Ia), whether obtained by Method A or Method B, can be converted to other compounds of the invention, for example by the following Methods.

METHOD C

Compounds of formula (Ia) in which any one or more of $R^{1'}$, $R^{2'}$, $R^{3'}$, $R^{4'}$ or Y' represents an alkyl or aralkyl group can be prepared by reacting the corresponding compound of formula (Ia) in which $R^{1'}$, $R^{2'}$, $R^{3'}$, $R^{4'}$ or Y' represents a hydrogen atom with a compound of formula (XII):

$$R^5 \text{—} Q \qquad (XII)$$

(in which $R^5$ represents a $C_1$-$C_{18}$ alkyl group or an aralkyl group optionally having at least one $C_1$-$C_4$ alkyl or halogen substituent; and Q represents a halogen atom, for example a chlorine, bromine or iodine atom).

In this reaction, by appropriate selection of the reaction conditions, it is possible to convert $R^{1'}$ and Y' to the chosen alkyl or aralkyl group in a first step, whilst leaving hydrogen atoms represented by $R^{2'}$, $R^{3'}$ and $R^{4'}$ unaffected, and then convert these in a second step to an alkyl or aralkyl group, which may be the same as or different from the group to which $R^{1'}$ and Y' have been converted.

The reaction may be carried out in the presence or absence of an inert solvent and in the presence or absence of an acid-acceptor. Suitable acid-acceptors include alkali metal hydroxides and carbonates, such as sodium hydroxide, potassium hydroxide, sodium carbonate or potassium carbonate. Suitable inert solvents include, for example: ethers, such as dioxane, tetrahydrofuran or diethyl ether; aromatic hydrocarbons, such as benzene, toluene or xylene; alcohols, such as methanol, ethanol or propanol; amides, such as dimethylformamide, dimethylacetamide or hexamethylphosphoric triamide; and mixtures of one or more of these solvents with water.

The reaction temperature is preferably within the range from room temperature to 150° C. and the time required for the reaction is generally from 30 minutes to 3 hours.

Method D

Compounds of formula (Ia) in which one or more of $R^{1'}$, $R^{2'}$, $R^{3'}$, $R^{4'}$ and Y' represents a methyl group can be prepared by subjecting the corresponding compound of formula (Ia) in which $R^{1'}$, $R^{2'}$, $R^{3'}$, $R^{4'}$ or Y' represents a hydrogen atom to a Leuckart-Wallach reaction. This reaction may be carried out by reacting the compound of formula (Ia) with formaldehyde and formic acid in water at a temperature from 50° C. to 100° C. The time required for the reaction is generally from 5 hours to 20 hours.

METHOD E

Compounds of formula (Ia) in which one or more of $R^{1'}$, $R^{2'}$, $R^{3'}$, $R^{4'}$ and Y' represents a hydrogen atom can be converted to the corresponding compound of formula (I) in which one or more of $R^1$, $R^2$, $R^3$, $R^4$ and Y represents an acyl group by a conventional acylation reaction.

This reaction may be effected by reacting the compound of formula (Ia) with an appropriate amount of an active derivative of the corresponding carboxylic acid, particularly an acid halide, acid anhydride or lower (e.g. $C_1$-$C_4$) alkyl ester of the acid.

When an acid halide or acid anhydride is used, $R^{1'}$ and Y' of compound (Ia) are the first to be converted to an acyl group, after which $R^{2'}$, $R^{3'}$ and $R^{4'}$ are converted in a second step. Clearly, by appropriate selection of the reaction conditions, it is possible to carry out these two steps using different acylating agents and thus introducing different acyl groups. However, it is generally more convenient and desirable to acylate all reactive positions together in a single stage. When a lower alkyl ester is used as the acylating agent, only $R^{1'}$ and Y' undergo reaction.

The reaction using an acid halide may be effected in the presence or absence of an acid-acceptor and is preferably carried out in an inert solvent at a temperature from room temperature to 130° C. Depending upon the reaction conditions, the time required for the reaction will generally range from 30 minutes to 3 hours.

Suitable acid-acceptors include: alkali metal hydroxides and carbonates, such as sodium hydroxide, potassium hydroxide, sodium carbonate or potassium carbonate; and organic amines, such as triethylamine or pyridine. Suitable inert solvents include: aromatic hydrocarbons, such as benzene, toluene or xylene; halogenated aliphatic hydrocarbons, such as methylene chloride, chloroform or trichloroethane; and ethers, such as diethyl ether, tetrahydrofuran or dioxane.

The reaction using an acid anhydride may be carried out in the presence of an inert solvent or, by using an excess of acid anhydride, in the absence of an inert solvent. Suitable inert solvents include: aromatic hydrocarbons, such as benzene, toluene or xylene; and ethers, such as dioxane, tetrahydrofuran or diethylene glycol diethyl ether. The reaction is preferably effected at a temperature from room temperature to 160° C. and the time required for the reaction will generally be from 30 minutes to 20 hours.

The acylation reaction using a lower alkyl ester of the acid is preferably effected in the presence of a base and an inert solvent, whilst continuously removing the lower alcohol produced.

Suitable bases include, for example: alkali metal compounds, such as sodium methoxide, sodium ethoxide, potassium t-butyoxide sodium hydroxide, potassium hydroxide or lithium amide; and titanates, such as tetraisopropyl titanate or tetrabutyl titanate. Of these, sodium ethoxide, potassium hydroxide and lithium amide are preferred. Suitable inert solvents include, for example, hydrocarbons, such as benzene, toluene, xylene, heptane, octane, isooctane, cyclohexane or ethylcyclohexane.

The reaction is preferably effected at a temperature of from 80° to 180° C. and the time required for the reaction is normally from 30 minutes to 5 hours.

After completion of any of the above Methods, the desired products may be separated from the reaction mixture by conventional means. For example, one suitable recovery technique comprises: if necessary, filtering insoluble matter from the reaction mixture; if the reaction mixture is acidic or alkaline, neutralising it; adding water to the mixture; extracting the product with a water-immiscible organic solvent; drying the extract; and then distilling the solvent from the extract to give the desired product. If necessary, this product may be purified, for example by column chromatography, preparative thin layer chromatography, distillation or recrystallisation.

The compounds of the invention are readily compatible with most organic polymers and have a relatively low volatility and tendency to migrate. They are effective stabilizers against light and heat and are effective against gaseous degradation and can, accordingly, be used for a wide range of synthetic polymers.

Examples of polymers which can be stabilized by the compounds of the invention include the following:

Olefin and Diene polymers

Homopolymers of olefins or dienes, for example, polyethylene (which can be low density, linear-chain low density, high density or crosslinked), polypropylene, polyisobutylene, polybutene-1, polymethylbutene-1, polymethylpentene-1, polyisoprene or polybutadiene. Mixtures of two or more of the homopolymers mentioned above, for example, mixtures of polypropylene with polyethylene, with polybutene-1 or with polyisobutylene. Copolymers of olefins and dienes, for example, ethylene/propylene copolymers, propylene/butene-1 copolymers, propylene/isobutene copolymers, ethylene/butene-1 copolymers and also terpolymers of ethylene with propylene and a diene (e.g. hexadiene, dicyclopentadiene or ethylidenenorbornene).

Styrene polymers

Polystyrene, and copolymers of styrene or alpha-methylstyrene (for example, styrene-butadiene copolymer, styrene-acrylonitrile copolymer, styrene-acrylonitrile-methyl methacrylate copolymer, styrene-acrylonitrile-acrylate copolymer, styrene-acrylonitrile copolymer denatured with a polyacrylate in order to give a high impact strength or styrene polymer denatured with an EPDM in order to give a high impact strength). Graft copolymers of styrene, for example, styrene on polybutadiene, styrene and acrylonitrile on polybutadiene and mixtures thereof with the above copolymers, such as those known as ABS polymers.

Halogen-containing polymers

Polyvinyl chloride, polyvinylidene chloride, polyvinyl fluoride, polychloroprene, chlorinated rubbers, chlorinated polyethylene, vinyl chloride-vinylidene chloride copolymer, vinyl chloride-vinyl acetate copolymer and vinylidene chloride-vinyl acetate copolymer.

Polymers which are derived from alpha,beta-unsaturated acids and their derivatives Polyacrylates, polymethacrylates, polyacrylamides and polyacrylonitrile, Polymers which are derived from unsaturated alcohols and amines or their acyl derivatives or acetals Polyvinyl alcohol, polyvinyl acetate, polyvinyl stearate, polyvinyl benzoate, polyvinyl maleate, polyvinyl butyral, polyallyl phthalate, polyallyl melamine and their copolymers with other vinyl compounds, such as ethylene-vinyl acetate copolymers.

Epoxy polymers

Homo- and co-polymers of epoxides, such as polyethylene oxide and their copolymers with bis-glycidyl ethers.

Polyacetals, polyalkylene oxides and polyphenylene oxides

Polyoxymethylene, oxymethylene-ethylene oxide copolymer, polyoxyethylene, polypropylene oxide, polyisobutylene oxide and polyphenylene oxide.

Polyurethanes and polyureas

Polycarbonates

Polysulphones

Polyamides and copolyamides

Polyamides and copolyamides which are derived from diamines and aliphatic or aromatic dicarboxylic acids and/or from aminocarboxylic acids or the corresponding lactams such as Nylon 6, Nylon 6/6, Nylon 6/10, Nylon 11 and Nylon 12.

Polyesters

Polyesters which are derived from dicarboxylic acids and dialcohols and/or from hydroxycarboxylic acids or the corresponding lactones such as polyethylene terephthalate, polybutylene terephthalate and polycyclohexane-1,4-dimethyleneterephthalate.

Crosslinked polymers

Crosslinked polymers which are derived from (a) an aldehyde and from (b) a phenol, urea or melamine, such as phenol-formaldehyde resins, urea-formaldehyde resins and melamine-formaldehyde resins, and diallylphthalate resins.

Alkyd resins

Glycerol/phthalic acid resins and their mixtures with melamine-formaldehyde resins.

Unsaturated polyester resins

Derived from copolymers of saturated and unsaturated dicarboxylic acids with polyhydric alcohols and a vinyl compound as the crosslinking agent and also their halogen-containing modifications of low combustibility.

The amount of compound of the invention employed as a stabilizer will depend upon various factors, for example the nature and properties of the polymer, the intended use of the polymer composition and whether or not there are any other stabilizers present. In general, however, the stabilizers will be added to the polymers in an amount of from 0.01 to 5% by weight, based on the weight of the polymer. However, the most effective amount of stabilizer depends upon the nature of the polymer and specifically:

For olefin, diene and styrene polymers, we prefer to use from 0.01 to 2.0% by weight of stabilizer, based on the polymer, more preferably from 0.02 to 1% by weight.

For polymers derived from vinyl chloride or vinylidene chloride, we prefer to use from 0.01 to 1.0% by weight of stabilizer, based on the weight of the polymer, more preferably from 0.02 to 0.5% by weight.

For polyurethanes and polyamides, we prefer to use from 0.01 to 5.0% by weight of stabilizer, based on the weight of polymer, more preferably from 0.02 to 2.0% by weight.

If desired, two or more of the compounds of the invention may be used together as stabilizers and, if desired, other stabilizers may be used in combination with one or more of the stabilizers of the invention.

The stabilizers of the invention can easily be mixed, employing conventional techniques, into the polymer or prepolymer at any suitable stage prior to preparation of shaped articles or other products from the polymer compositions. For example, the stabilizers may be mixed into the polymer in the molten condition or as dry pulverized materials or a suspension or emulsion of the stabilizer or stabilizers may be mixed with a solution, suspension or emulsion of the polymer.

It is possible to incorporate other additives commonly employed in polymer technology into the stabilized polymer compositions of the invention. Examples of such additives are disclosed in U.K. Patent Specification No. 1,401,924, incorporated herein by reference.

Polymers stabilized in this way can be employed in very many different forms, for examples as films, fibres, tapes, compression-moulding compositions, coating compositions or paints.

The preparation and use of compounds of the present invention is further illustrated by the following Examples, whilst the preparation of certain materials for use in the Examples is illustrated in the following Preparations. Parts and percentages are given by weight.

PREPARATION 1

(a) 4-Butylamino-2,2,6,6-tetramethylpiperidine 2.0 g of platinum oxide were added to a solution of 155 g of 2,2,6,6-tetramethyl-4-piperidone and 80 g of butylamine in 300 ml of methanol. The resulting mixture was then hydrogenated under a hydrogen atmosphere in a Parr hydrogenation apparatus at room temperature for 5 hours. After completion of the reaction, the platinum catalyst was filtered off and the solvent was distilled from the filtrate under reduced pressure. The residue was purified by vacuum distillation, to give the desired product as an oil, boiling at 100°–101° C./5 mmHg (667 Pascals).

(b) 2-Chloro-4,6-bis[N-butyl-N-(2,2,6,6-tetramethyl-4-piperidyl)amino]-1,3,5-triazine To a solution of 18.4 g of cyanuric chloride in 200 ml of dioxane was added dropwise, with stirring, a solution of 43.6 g of 4-butylamino-2,2,6,6-tetramethylpiperidine in 100 ml of dioxane at 20°–25° C. The mixture was stirred at the same temperature for 2 hours, after which it was stirred at 60°–70° C. for 2 hours. At the end of this time, the dioxane was distilled off and the residue was poured into a 10% aqueous solution of potassium carbonate and extracted with ethyl acetate. The extract was dried over anhydrous potassium carbonate, and then the ethyl acetate was distilled off. The resulting oil was purified by column chromatography through silica gel, eluted with a 20:1:1 by volume mixture of ethyl acetate, ethanol and triethylamine, to give the title compound in the form of crystals melting at 40°–42° C.

PREPARATION 2

(a) 2,2,6,6-Tetramethyl-4-(octylamino)piperidine

The procedure described in Preparation 1(a) was repeated, but replacing the butylamine by octylamine, to give the title compound, boiling at 143°–146° C./3 mmHg (400 Pascals).

(b) 2-Chloro-4,6-bis[N-octyl-N-(2,2,6,6-tetramethyl-4-piperidyl)amino]-1,3,5-triazine The procedure described in Preparation 1(b) was repeated, but employing as starting material the product of Preparation 2(a), to give the title compound as a pale yellow oil. The Rf value of this compound was 0.36 on thin layer chromatography using silica gel developed with a 20:1:1 by volume mixture of ethyl acetate, ethanol and triethylamine.

PREPARATION 3

(a) 4-Dodecylamino-2,2,6,6-tetramethylpiperidine 1.0 g of platinum oxide was added to a solution of 31.0 g of 2,2,6,6-tetramethyl-4-piperidone and 47.0 g of dodecylamine in 250 ml of methanol. The resulting mixture was then hydrogenated under a hydrogen atmosphere in a Parr hydrogenation apparatus at room temperature for 3 hours. After completion of the reaction, the platinum catalyst was filtered off, and then the solvent was distilled from the filtrate under reduced pressure to give an oily product. This product was purified by column chromatography through silica gel, eluted with a 20:3:1 by volume mixture of ethyl acetate, ethanol and triethylamine, to give the title compound as an oil. The Rf value of this product on thin layer chromatography was 0.34, using silica gel and a 20:3:1 by volume mixture of ethyl acetate, ethanol and triethylamine as the developing solvent.

(b) 2-Chloro-4,6-bis[N-dodecyl-N-(2,2,6,6-tetramethyl-4-piperidyl)amino]-1,3,5-triazine A solution of 35.7 g of 4-dodecylamino-2,2,6,6-tetramethylpiperidine in 50 ml of xylene was added dropwise at 20°–25° C. to a solution of 9.2 g of cyanuric chloride in 250 ml of xylene. The mixture was stirred for 1.5 hours at the same temperature and then for 5 hours at 50°–55° C. At the end of this time, the reaction mixture was neutralised with an aqueous solution of potassium carbonate, and the xylene layer was separated and dried over anhydrous potassium carbonate. The xylene was distilled off and the resulting oil was purified by column chromatography through silica gel eluted with a 20:20:3:1 by volume mixture of ethyl acetate, benzene, ethanol and triethylamine to give the title compound as an oil. The Rf value of this compound on thin layer chromatography was 0.28, using silica gel and using, as developing solvent, a 20:20:3:1 by volume mixture of ethyl acetate, benzene, ethanol and triethylamine.

PREPARATION 4

(a) 4-(2-Ethylhexylamino)-2,2,6,6-tetramethylpiperidine

The procedure described in Preparation 1(a) was repeated but employing 2-ethylhexylamine in place of the butylamine, to give the title compound, boiling at 108°–110° C./1 mmHg (133 Pascals).

(b) 2-Chloro-4,6-bis[N-(2-ethylhexyl)-N-(2,2,6,6-tetramethyl-4-piperidyl)amino]-1,3,5-triazine A suspension of 9.2 g of cyanuric chloride in 60 ml of acetone and 20 ml of water was added dropwise, with stirring, at 20°–25° C. to a solution of 29.5 g of 4-(2-ethylhexylamino)-2,2,6,6-tetramethylpiperidine in 50 ml of acetone, after which a solution of 4.2 g of sodium hydroxide in 20 ml of water was added to the mixture. The resulting reaction mixture was then stirred for 4 hours at 45°–50° C. At the end of this time, the acetone was distilled off and the oily residue was extracted with ethyl acetate. The extract was dried over anhydrous potassium carbonate, and the ethyl acetate was distilled off. The resulting oil was purified by column chromatography through silica gel, eluted with a 4:1 by volume mixture of hexane and ethyl acetate, to give the title compound as a colourless oil. The Rf value of this compound on thin layer chromatography was 0.62, using silica gel and using, as developing solvent, a 4:1:0.4 by volume mixture of ethyl acetate, methanol and triethylamine.

PREPARATION 5

(a) 2,2,6,6-Tetramethyl-4-(octadecylamino)piperidine

The procedure described in Preparation 3(a) was repeated, but employing octadecylamine in place of dodecylamine, to give the title compound as an oil. The Rf value of this compound on thin layer chromatography was 0.27, using silica gel and using, as developing solvent, a 20:3:1 by volume mixture of ethyl acetate, ethanol and triethylamine.

(b) 2-Chloro-4,6-bis[N-octadecyl-N-(2,2,6,6-tetramethyl-4-piperidyl)amino]-1,3,5-triazine A solution of 12.0 g of cyanuric chloride in 100 ml of xylene was added dropwise at 20°–25° C. to a solution of 54.0 g of 2,2,6,6-tetramethyl-4-(octadecylamino)-piperidine in 200 ml of xylene. The resulting mixture was then heated under reflux for 8 hours, after which it was neutralised with an aqueous solution of potassium carbonate and then extracted with benzene. The extract was dried over anhydrous potassium carbonate and then the solvent was distilled off. The resulting residue was purified by column chromatography through silica gel, eluted with a 20:1:1 by volume mixture of ethyl acetate, ethanol and triethylamine, to give the title compound in the form of crystals. These were recrystallised from ethyl acetate, giving the purified title compound in the form of colourless crystals melting at 68°–70° C.

PREPARATION 6

(a) 4-(3-Methoxypropylamino)-2,2,6,6-tetramethylpiperidine

The procedure described in Preparation 1(a) was repeated, but employing 3-methoxypropylamine in place of the butylamine, to give the title compound, boiling at 110°–111° C./4 mmHg (533 Pascals).

(b) 2-Chloro-4,6-bis[N-(3-methoxypropyl)-N-(2,2,6,6-tetramethyl-4-piperidyl)amino]-1,3,5-triazine The procedure described in Preparation 3(b) was repeated, but employing as starting material the product of Preparation 6(a), to give the title compound in the form of an oil. This was purified by column chromatography through silica gel, eluted with a 20:3:1 by volume mixture of ethyl acetate, ethanol and triethylamine, to give the title compound in the form of crystals, melting at 160°–161° C.

PREPARATION 7

(a) 4-(3-Ethoxypropylamino)-2,2,6,6-tetramethylpiperidine

The procedure of Preparation 1(a) was repeated, but employing 3-ethoxypropylamine in place of the butylamine, to give the title compound, boiling at 114°–116° C./2 mmHg (267 Pascals).

(b) 2-Chloro-4,6-bis[N-(3-ethoxypropyl)-N-(2,2,6,6-tetramethyl-4-piperidyl)amino]-1,3,5-triazine The procedure described in Preparation 4(b) was repeated, to give the title compound in the form of an oil, which was further purified by chromatography. The Rf value on thin layer chromatography of this compound was 0.34, using silica gel and using, as developing solvent, a 8:1:0.2 by volume mixture of ethyl acetate, methanol and triethylamine.

PREPARATION 8

(a) 2,2,6,6-Tetramethyl-4-(propylamino)piperidine

The procedure described in Preparation 1(a) was repeated, but employing propylamine in place of the butylamine, to give the title compound boiling at 83°–84° C./3.5 mmHg (467 Pascals).

(b) 2-Chloro-4,6-bis[N-propyl-N-(2,2,6,6-tetramethyl-4-piperidyl)amino]-1,3,5-triazine The procedure described in Preparation 1(b) was repeated, but employing as starting material the product of Preparation 8(a), to give the title compound in the form of crystals melting at 141.5°–143° C.

PREPARATION 9

(a) 4-Amino-2,2,6,6-tetramethylpiperidine

The procedure described in Preparation 1(a) was repeated, but employing ammonia in place of the butylamine, to give the title compound, boiling at 102°–104° C./26 mmHg (3466 Pascals).

(b) 2-Chloro-4,6-bis[N-(2,2,6,6-tetramethyl-4-piperidyl)amino]-1,3,5-triazine

The procedure described in Preparation 5(b) was repeated, but using the product of Preparation 9(a) as the starting material, to give the title compound in the form of a raw material, which, on recrystallization from ethanol, gave crystals melting at 276°–277° C.

PREPARATION 10

(a) 4-Amino-1,2,2,6,6-pentamethylpiperidine

The procedure described in Preparation 1(a) was repeated, but using as starting materials 1,2,2,6,6-pentamethyl-4-piperidone and ammonia, to give the title compound, boiling at 76°–79.5° C./5 mmHg (667 Pascals).

(b) 2-Chloro-4,6-bis[N-(1,2,2,6,6-pentamethyl-4-piperidyl)amino]-1,3,5-triazine 9.0 g of cyanuric chloride and 20.0 g of 4-amino-1,2,2,6,6-pentamethylpiperidine were dissolved in 100 ml of xylene, and the solution was stirred at room temperature for 1 hour. 50 ml of a saturated aqueous solution of potassium carbonate were then added to the resulting solution and the mixture was stirred for a further 2 hours at 60° C. At the end of this time, water and chloroform were added to the mixture, which was then allowed to stand at room temperature. The resulting crystals were filtered off and then recrystallized from benzene, to give the title compound in the form of crystals melting at 290° C.

PREPARATION 11

(a) 2,2,6,6-Tetramethyl-4-(methylamino)piperidine

The procedure described in Preparation 1(a) was repeated, but employing methylamine in place of butylamine, to give the title compound, boiling at 68°–70° C./3.5 mmHg (467 Pascals).

(b) 2-Chloro-4,6-bis[N-methyl-N-(2,2,6,6-tetramethyl-4-piperidyl)amino]-1,3,5-triazine 18.4 g of cyanuric chloride and 34.0 g of 2,2,6,6-tetramethyl-4-(methylamino)piperidine were dissolved in 250 ml of xylene, and the solution was stirred at a temperature of 90°–110° C. for 3 hours. 30 ml of a saturated aqueous solution of potassium carbonate were then added and the resulting mixture was heated under reflux for 5 hours. At the end of this time, the reaction mixture was poured into water and extracted with benzene. The extract was dried over anhydrous potassium carbonate and then the benzene was distilled off. The residue was recrystallized from ethyl acetate, giving the title compound in the form of crystals melting at 179°–180° C.

PREPARATION 12

(a) Bis(2,2,6,6-tetramethyl-4-piperidyl)amine 1.0 g of platinum oxide was added to a suspension of 50.0 g of 2,2,6,6-tetramethyl-4-piperidone and 109 g of ammonium chloride in 200 ml of methanol. The resulting mixture was then hydrogenated in a hydrogen atmosphere, employing a Parr hydrogenation apparatus at room temperature for 8 hours. At the end of this time, the reaction mixture was poured into an aqueous solution of potassium carbonate. The platinum catalyst was filtered off and the filtrate was extracted with benzene. The extract was dried over anhydrous potassium carbonate and then the benzene was distilled off. The resulting oil was distilled under a high vacuum, to give the title compound in the form of an oil boiling at 135°–139° C./2 mmHg (267 Pascals). This product was purified by column chromatography through silica gel, eluted with a 5:5:1 by volume mixture of ethyl acetate, ethanol and triethylamine, to give the title compound in the form of crystals melting at 77°–78° C.

(b) 2-Chloro-4,6-bis[N,N-bis(2,2,6,6-tetramethyl-4-piperidyl)amino]-1,3,5-triazine Following the procedure described in Preparation 11(b), cyanuric chloride was reacted with bis(2,2,6,6-tetramethyl-4-piperidyl)amine [prepared as described in Preparation 12(a)]. After completion of the reaction, the reaction mixture was poured into water and extracted with chloroform. The extract was dried over anhydrous potassium carbonate and then the chloroform was distilled off. The residue was recrystallized from chloroform, to afford the desired product, in the form of crystals melting at 295° C. (with decomposition).

EXAMPLE 1

1,8-Bis[N-(2,4-bis[N-butyl-N-(2,2,6,6-tetramethylpiperid-4-yl)amino]-1,3,5-triazin-6-yl)amino]-4-[N-(2,4-bis[N-butyl-N-(2,2,6,6-tetramethylpiperid-4-yl)amino]-1,3,5-triazin-6-yl)aminomethyl]octane (Compound No. 7)

14.9 g of 2-chloro-4,6-bis[N-butyl-N-(2,2,6,6-tetramethyl-4-piperidyl)amino]-1,3,5-triazine [obtained as described in Preparation 1(b)] and 1.3 g of 1,8-diamino-4-aminomethyloctane were dissolved in 200 ml of xylene, and the solution was heated under reflux for 22 hours. At the end of this time, a solution of 3.9 g of potassium carbonate in 10 ml of water was added to the reaction mixture and stirred for 30 minutes. The xylene layer was then separated and dried over anhydrous potassium carbonate, after which the xylene was distilled off. The residue was purified by column chromatography through silica gel, eluted with a 20:3:1 by volume mixture of ethyl acetate, ethanol and triethylamine, to give the desired Compound No. 7, in the form of crystals melting at 103°–105° C.

EXAMPLE 2

1,8-Bis[N-(2,4-bis[N-octyl-N-(2,2,6,6-tetramethylpiperid-4-yl)amino]-1,3,5-triazin-6-yl)amino]-4-[N-(2,4-bis[N-octyl-N-(2,2,6,6-tetramethylpiperid-4-yl)amino]-1,3,5-triazin-6-yl)aminomethyl]octane (Compound No. 14)

A solution of 28.3 g of 2-chloro-4,6-bis[N-octyl-N-(2,2,6,6-tetramethyl-4-piperidyl)amino]-1,3,5-triazine [prepared as described in Preparation 2(b)] and 1.0 g of 1,8-diamino-4-aminomethyloctane in 200 ml of xylene was refluxed for 10 hours. It was then treated as described in Example 1 to give a residue, which was purified by column chromatography through silica gel, eluted with a 20:1:1 by volume mixture of ethyl acetate, ethanol and triethylamine, to give the desired Compound No. 14, in the form of crystals melting at 55°–60° C.

EXAMPLE 3

1,8-Bis[N-(2,4-bis[N-propyl-N-(2,2,6,6-tetramethylpiperid-4-yl)amino]-1,3,5-triazin-6-yl)amino]-4-[N-(2,4-bis[N-propyl-N-(2,2,6,6-tetramethylpiperid-4-yl)amino]-1,3,5-triazin-6-yl)aminomethyl]octane (Compound No. 6)

Following the procedure described in Example 1, the desired Compound No. 6 was obtained, in the form of crystals melting at 137°–140° C., from 2-chloro-4,6-bis[N-propyl-N-(2,2,6,6-tetramethyl-4-piperidyl)amino]-1,3,5-triazine [obtained as described in Preparation 8(b)] and 1,8-diamino-4-aminomethyloctane.

EXAMPLE 4

1,8-Bis[N-(2,4-bis[N-dodecyl-N-(2,2,6,6-tetramethylpiperid-4-yl)amino]-1,3,5-triazin-6-yl)amino]-4-[N-(2,4-bis[N-dodecyl-N-(2,2,6,6-tetramethylpiperid-4-yl)amino]-1,3,5-triazin-6-yl)aminomethyl]octane (Compound No. 21)

Following the procedure described in Example 2, the desired Compound No. 21 was obtained, as an oil, from 2-chloro-4,6-bis[N-dodecyl-N-(2,2,6,6-tetramethyl-4-piperidyl)amino]-1,3,5-triazine [obtained as described in Preparation 3(b)] and 1,8-diamino-4-aminomethyloctane. The Rf value of the product on thin layer chromatography was 0.24, using silica gel and using, as developing solvent, a 20:3:1 by volume mixture of ethyl acetate, ethanol and triethylamine.

EXAMPLE 5

1,8-Bis[N-(2,4-bis[N-(2-ethylhexyl)-N-(2,2,6,6-tetramethylpiperid-4-yl)amino]-1,3,5-triazin-6-yl)amino]-4-[N-(2,4-bis[N-(2-ethylhexyl)-N-(2,2,6,6-tetramethylpiperid-4-yl)amino]-1,3,5-triazin-6-yl)aminomethyl]octane (Compound No. 18)

Following the procedure described in Example 1, 2-chloro-4,6-bis[N-(2-ethylhexyl)-N-(2,2,6,6-tetramethyl-4-piperidyl)amino]-1,3,5-triazine [obtained as described in Preparation 4(b)] and 1,8-diamino-4-aminomethyloctane were reacted together and the product treated to give a residue. This residue was purified by column chromatography through silica gel, eluted with a 20:5:2 by volume mixture of ethyl acetate, methanol and triethylamine, to give the desired Compound No. 18, in the form of crystals melting at 55°–60° C.

EXAMPLE 6

1,8-Bis[N-(2,4-bis[N-octadecyl-N-(2,2,6,6-tetramethylpiperid-4-yl)amino]-1,3,5-triazin-6-yl)amino]-4-[N-(2,4-bis[N-octadecyl-N-(2,2,6,6-tetramethylpiperid-4-yl)amino]-1,3,5-triazin-6-yl)aminomethyl]octane (Compound No. 24)

Following the procedure described in Example 1, 2-chloro-4,6-bis[N-octadecyl-N-(2,2,6,6-tetramethyl-4-piperidyl)amino]-1,3,5-triazine [prepared as described in Preparation 5(b)] and 1,8-diamino-4-aminomethyloctane were reacted together and the reaction mixture treated to give a residue. This residue was subjected to column chromatography through silica gel, eluted with a 10:5:5:1 by volume mixture of hexane, benzene, ethyl acetate and triethylamine, to give the desired Compound No. 24 in the form of an oil. The Rf value of this product on thin layer chromatography was 0.43, using silica gel and using, as developing solvent, a 4:4:4:1 by volume mixture of hexane, benzene, ethyl acetate and triethylamine.

EXAMPLE 7

1,8-Bis[N-(2,4-bis[N-(3-methoxypropyl)-N-(2,2,6,6-tetramethylpiperid-4-yl)amino]-1,3,5-triazin-6-yl)amino]-4-[N-(2,4-bis[N-(3-methoxypropyl)-N-(2,2,6,6-tetramethylpiperid-4yl)amino]-1,3,5-triazin-6-yl)aminomethyl]octane (Compound No. 32)

Following the procedure described in Example 1, 2-chloro-4,6-bis[N-(3-methoxypropyl)-N-(2,2,6,6-tetramethyl-4-piperidyl)amino]-1,3,5-triazine [prepared as described in Preparation 6(b)] and 1,8-diamino-4-aminomethyloctane were reacted together and the reaction mixture treated to yield a residue, which was purified by column chromatography through silica gel, eluted with 4:1:1 by volume mixture of ethyl acetate, ethanol and triethylamine, to give the desired Compound No. 32, in the form of crystals melting at 96°–99° C.

EXAMPLE 8

1,8Bis[N-(2,4-bis[N-(3-ethoxypropyl)-N-(2,2,6,6-tetramethylpiperid-4-yl)amino]-1,3,5-triazin-6-yl)amino]-4-[N-(2,4-bis[N-(3-ethoxypropyl)-N-(2,2,6,6-tetramethylpiperid-4-yl)amino]-1,3,5-triazin-6-yl)aminomethyl]octane (Compound No. 35)

Following the procedure described in Example 1, 2-chloro-4,6-bis[N-(3-ethoxypropyl)-2,2,6,6-tetramethyl-4-piperidyl)amino]-1,3,5-triazine [prepared as described in Preparation 7(b)] and 1,8-diamino-4-aminomethyloctane were reacted together and the reaction mixture treated to give a residue, which was then subjected to column chromatography through silica gel, eluted with 30:5:1 by volume mixture of ethyl acetate, methanol and triethylamine, to give the desired Compound No. 35, in the form of crystals melting at 80°–82° C.

EXAMPLE 9

1,8-Bis[N-(2,4-bis[N-methyl-N-(2,2,6,6-tetramethylpiperid-4-yl)amino]-1,3,5-triazin-6-yl)amino]-4-[N-(2,4-bis[N-methyl-N-(2,2,6,6-tetramethylpiperid-4-yl)amino]-1,3,5-triazin-6-yl)aminomethyl]octane (Compound No. 3)

10 ml of a saturated aqueous solution of potassium carbonate were added to a solution of 9.0 g of 2-chloro-4,6-bis[N-methyl-N-(2,2,6,6-tetramethyl-4-piperidyl)amino]-1,3,5-triazine [prepared as described in Preparation 11(b)] and 0.89 g of 1,8-diamino-4-aminomethyloctane in 10 ml of xylene. The mixture was then refluxed for 8 hours, after which it was poured into water and extracted with benzene. The extract was dried over anhydrous potassium carbonate, and then the solvent was distilled off. The residue was subjected to column chromatography through silica gel, eluted with a 20:3:1 by volume mixture of ethyl acetate, ethanol and triethylamine, to give the desired Compound No. 3, in the form of crystals melting at 152°–157° C.

EXAMPLE 10

1,8-Bis(N-[2,4-bis(2,2,6,6-tetramethylpiperid-4-ylamino)-1,3,5-triazin-6-yl]amino)-4-(N-[2,4-bis(2,2,6,6-tetramethylpiperid-4-ylamino)-1,3,5-triazin-6-yl]aminomethyl)octane (Compound No. 1)

5.1 g of 2-chloro-4,6-bis[N-(2,2,6,6-tetramethyl-4-piperidyl)amino]-1,3,5-triazine [prepared as described in Preparation 9(b)] were reacted with 0.7 g of 1,8-diamino-4-aminomethyloctane, following the procedure described in Example 9. After completion of the reaction, the reaction mixture was poured into water and extracted with chloroform. The extract was dried over anhydrous potassium carbonate, and the solvent was distilled off. The residue was purified by column chromatography through silica gel, eluted with a 8:2:1 by volume mixture of ethyl acetate, ethanol and triethylamine, to give the desired Compound No. 1 in the form of crystals melting at 148°–158° C.

EXAMPLE 11

1,8-Bis(2,4-bis[N,N-bis(2,2,6,6-tetramethylpiperid-4-yl)amino]-1,3,5-triazin-6-ylamino)-4-[N-(2,4-bis[N,N-bis(2,2,6,6-tetramethylpiperid-4-yl)amino]-1,3,5-triazin-6-yl)aminomethyl]octane (Compound No. 41)

A mixture of 20.8 g of 2-chloro-4,6-bis[N,N-bis(2,2,6,6-tetramethyl-4-piperidyl)amino]-1,3,5-triazine [prepared as described in Preparation 12(b)], 1.3 g of 1,8-diamino-4-aminomethyloctane and 4.5 g of potassium carbonate was heated at 170°–190° C., with stirring, for 12 hours. At the end of this time, the reaction mixture was poured into water and then extracted with chloroform. The extract was dried over anhydrous potassium carbonate and the chloroform was distilled off. The residue was purified by column chromatography through silica gel, eluted with 5:5:1 by volume mixture of ethyl acetate, ethanol and triethylamine, to give the desired Compound No. 41, in the form of crystals melting at 200°–205° C.

EXAMPLE 12

1,8-Bis(N-[2,4-bis(1,2,2,6,6-pentamethylpiperid-4-ylamino)-1,3,5-triazin-6-yl]amino)-4-(N-[2,4-bis(1,2,2,6,6-pentamethylpiperid-4-ylamino)-1,3,5-triazin-6-yl]aminoethyl)octane (Compound No. 2)

4.5 g of 2-chloro-4,6-bis[N-(1,2,2,6,6-pentamethyl-4-piperidyl)amino]-1,3,5-triazine [prepared as described in Preparation 10(b)] and 0.5 g of 1,8-diamino-4-aminomethyloctane were reacted together and the reaction mixture was treated as described in Example 9, to give a residue. This residue was purified by column chromatography through silica gel, eluted with a 5:5:2 by volume mixture of ethyl acetate, ethanol and triethylamine, and then recrystallized from cyclohexane to give the desired compound No. 2, in the form of crystals melting at 160°–163° C.

EXAMPLE 13

1,8-Bis[N-methyl-N-(2,4-bis[N-butyl-N-(1,2,2,6,6-pentamethylpiperid-4-yl)amino]-1,3,5-triazin-6-yl)amino]-4-[N-methyl-N-(2,4-bis[N-butyl-N-(1,2,2,6,6-pentamethylpiperid-4-yl)amino[-1,3,5-triazin-6-yl)aminomethyl]octane (Compound No. 8)

A mixture of 5.6 g of 1,8-bis[N-(2,4-bis[N-butyl-N-(2,2,6,6-tetramethylpiperid-4-yl)amino]-1,3,5-triazin-6-yl)amino]-4-[N-(2,4-bis[N-butyl-N-(2,2,6,6-tetramethylpiperid-4-yl)amino]-1,3,5-triazin-6-yl)aminomethyl]octane (prepared as described in Example 1), 24.0 g of 37% formalin and 14.0 g of 98% formic acid was heated under reflux for 14 hours. After completion of the reaction, the reaction mixture was poured into ice-water. The resulting solution was made alkaline by the addition of sodium bicarbonate, and it was then extracted with benzene. The extract was dried over anhydrous potassium carbonate and then the solvent was distilled off. The resulting oily residue was purified by column chromatography through silica gel, eluted with a 20:40:1 by volume mixture of ethyl acetate, benzene and triethylamine, to give the desired Compound No. 8, in the form of crystals melting at 128°–130° C.

EXAMPLE 14

1,8-Bis[N-methyl-N-(2,4-bis[N-(3-methoxypropyl)-N-(1,2,2,6,6-pentamethylpiperid-4-yl)amino]-1,3,5-triazin-6-yl)amino]-4-[N-methyl-N-(2,4-bis[N-(3-methoxypropyl)-N-(1,2,2,6,6-pentamethylpiperid-4-yl)amino]-1,3,5-triazin-6-yl)aminomethyl]octane (Compound No. 33)

The procedure described in Example 13 was repeated but using 1,8-bis[N-(2,4-bis[N-(3-methoxypropyl)-N-(2,2,6,6-tetramethylpiperid-4-yl)amino]-1,3,5-triazin-6-yl)amino]-4-[N-(2,4-bis[N-(3-methoxypropyl)-N-(2,2,6,6-tetramethylpiperid-4-yl)amino]-1,3,5-triazin-6-yl)aminomethyl]octane (prepared as described in Example 7) as the starting material. The residue obtained after subsequent treatment of the reaction mixture was purified by column chromatography through silica gel, eluted with 20:1:1 by volume mixture of ethyl acetate, ethanol and triethylamine, to give the desired Compound No. 33, in the form of crystals melting at 117°–118° C.

EXAMPLE 15

1,8-Bis[N-acetyl-N-(2,4-bis[N-butyl-N-(1-acetyl-2,2,6,6-tetramethylpiperid-4-yl)amino]-1,3,5-triazin-6-yl)amino]-4-[N-acetyl-N-(2,4-bis[N-butyl-N-(1-acetyl-2,2,6,6-tetramethylpiperid-4-yl)amino]-1,3,5-triazin-6-yl)aminomethyl]octane (Compound No. 9)

6.0 g of 1,8-bis[N-(2,4-bis[N-butyl-N-(2,2,6,6-tetramethylpiperid-4-yl)amino]-1,3,5-triazin-6-yl)amino]-4-[N-(2,4-bis[N-butyl-N-(2,2,6,6-tetramethylpiperid-4-yl)amino]-1,3,5-triazin-6-yl)aminomethyl]octane (obtained as described in Example 1) and 2.0 g of acetic anyhydride were dissolved in 20 ml of pyridine, and the solution was heated at 100°–110° C. for 16 hours, with stirring. At the end of this time, the reaction mixture was poured into aqueous ammonia and extracted with benzene. The extract was dried over anhydrous potassium carbonate, and then the benzene was distilled off. The residue was purified by column chromatography through silica gel eluted with a 20:1:1 by volume mixture of ethyl acetate, ethanol and triethylamine, to give the desired Compound No. 9 in the form of crystals melting at 115°–118° C.

EXAMPLE 16

1,8-Bis[N-acetyl-N-(2,4-bis[N-(3-methoxypropyl)-N-(1-acetyl-2,2,6,6-tetramethylpiperid-4-yl)amino]-1,3,5-triazin-6-yl)amino]-4-[N-acetyl-N-(2,4-bis[N-(3-methoxypropyl)-N-(1-acetyl-2,2,6,6-tetramethylpiperid-4-yl)amino]-1,3,5-triazin-6-yl)aminomethyl]octane (Compound No. 34)

The procedure described in Example 15 was repeated, but using 1,8-bis[N-(2,4-bis[N-(3-methoxypropyl)-N-(2,2,6,6-tetramethylpiperid-4-yl)amino]-1,3,5-triazin-6-yl)amino]-4-[N-(2,4-bis[N-(3-methoxypropyl)-N-(2,2,6,6-tetramethylpiperid-4-yl)amino]-1,3,5-triazin-6-yl)aminomethyl]octane (prepared as described in Example 7) as the starting material, to give the desired Compound No. 34, in the form of crystals melting at 91°-94° C.

EXAMPLE 17

1,8-Bis[N-acetyl-N-(2,4-bis[N-octadecyl-N-(1-acetyl-2,2,6,6-tetramethylpiperid-4-yl)amino]-1,3,5-triazin-6-yl)amino]-4-[N-acetyl-N-(2,4-bis[N-octadecyl-N-(1-acetyl-2,2,6,6-tetramethylpiperid-4-yl)amino]-1,3,5-triazin-6-yl)aminomethyl]octane (Compound No. 26)

The procedure described in Example 15 was repeated, but using 1,8-bis[N-(2,4-bis[N-octadecyl-N-(2,2,6,6-tetramethylpiperid-4-yl)amino]-1,3,5-triazin-6-yl)amino]-4-[N-(2,4-bis[N-octadecyl-N-(2,2,6,6-tetramethylpiperid-4-yl)amino]-1,3,5-triazin-6-yl)aminomethyl]octane (prepared as described in Example 6), as starting material, to give an oily residue. This oily residue was purified by column chromatography through silica gel, eluted with a 5:5:5:1 by volume mixture of hexane, benzene, ethyl acetate and triethylamine, to give the desired Compound No. 26 in the form of an oil. The Rf value of this compound on thin layer chromatography was 0.45, using silica gel and using, as developing solvent, a 5:5:5:1 by volume mixture of hexane, benzene, ethyl acetate and triethylamine.

EXAMPLE 18

(a) Preparation of polymer test sheet 100 parts of unstabilized polypropylene powder (MFI-18), 0.2 part of the antioxidant stearyl 3-(3,5-di-t-butyl-4-hydroxyphenyl)propionate and 0.25 part of one of the stabilizer compounds of the present invention were kneaded for 10 minutes at 200° C. in a Brabender plastics kneader to give a homogeneous material. This material was then pressed to a sheet of thickness 2-3 mm in a laboratory press. A portion of this sheet was pressed for 6 minutes at 260° C. in a hydraulic press and then immediately placed into cold water to give a sheet of thickness 0.5 mm.

Following the same procedure, a 0.1 mm thick film was obtained from the 0.5 mm thick sheet. This film was cut into test pieces of dimensions 50×120 mm.

(b) Weathering test

The test specimens prepared in step (a) were exposed to the light of a Sunshine carbon-arc weather-meter at a black panel temperature of 63±3° C. The exposed films were subjected to tension tests at regular intervals and the times were recorded when the extension of the pieces decreased to 50% of the original extension. As controls, test specimens which were identical except that the stabilizer was omitted were subjected to the same test. The results are reported as a ratio in the following Table 1, the ratio being the time required for the extension of the test pieces to decrease to 50% divided by the time required for the extension of the controls to decrease to 50%.

In the following Table, the compound numbers are those assigned to the compounds of the invention in the foregoing list, whilst Compounds A and B are piperidyltriazine derivatives as disclosed in U.S. Pat. No. 4,108,829; specifically, Compound A is N,N',N''-tris(2,4-bis[N-butyl-N-(2,2,6,6-tetramethyl-4-piperidyl)amino]-1,3,5-triazin-6-yl)diethylenetriamine and Compound B is N,N'-bis(2,4-bis[N-butyl-N-(2,2,6,6-tetramethyl-4-piperidyl)amino]-1,3,5-triazin-6-yl)hexamethylenediamine; the same abbreviations are used in the subsequent Tables.

TABLE 1

| Compound No. | Ratio |
| --- | --- |
| 1 | 7.7 |
| 2 | 7.9 |
| 7 | 8.0 |
| 8 | 8.2 |
| 9 | 7.0 |
| 14 | 7.7 |
| 18 | 7.6 |
| 21 | 7.0 |
| 32 | 7.6 |
| 33 | 7.4 |
| Compound A | 5.7 |
| Compound B | 5.6 |
| No addition | 1.0 |

EXAMPLE 19

Resistance to heat

A 0.5 mm thick sheet of polypropylene, prepared as described in Example 18(a), was cut into test specimens of dimensions 10×100 mm. These specimens were placed into an oven at 150° C. and were periodically checked by bending them through 180° to determine the number of days before the pieces became brittle. The number of days is reported in Table 2.

TABLE 2

| Compound No. | Days |
| --- | --- |
| 1 | 8 |
| 2 | 11 |
| 7 | 12 |
| 8 | 10 |
| 9 | 9 |
| 14 | 10 |
| 18 | 10 |
| 21 | 10 |
| 32 | 12 |
| 33 | 13 |
| No addition | 4 |

EXAMPLE 20

(a) Preparation of test specimens 100 parts of low density polyethylene and 0.25 part of one of the stabilizers of the invention were kneaded together for 10 minutes at 180° C. in a Brabender plastics kneader, to give a homogeneous material. This material was pressed in a laboratory press to give a 2-3 mm thick sheet. A portion of the sheet was then pressed for 6 minutes at 160° C. in a hydraulic press, to give a 0.5 mm thick sheet. This sheet was cut into test specimens of dimensions 5×5 cm.

(b) Resistance to blooming

The test specimens were placed onto black cardboard and kept at room temperature. Every week they were examined to determine whether blooming had occurred. The number of weeks before blooming was observed is reported in Table 3. In those cases where the result is reported as "(16)", no blooming could be observed during the entire period of the test (16 weeks).

TABLE 3

| Compound No. | Weeks |
|---|---|
| 1 | (16) |
| 7 | 13 |
| 8 | 14 |
| 9 | 11 |
| 14 | 14 |
| 18 | 15 |
| 21 | (16) |
| 24 | 15 |
| 32 | (16) |
| Compound A | 2 |
| Compound B | 1 |

Low density polyethylenes have recently found use for various agricultural purposes and, for such purposes, compatibility of the stabilizers is very important because, since the permeability of the film to light decreases when the stabilizers bloom, this has a bad influence on the growth of crops. The results of the test reported in Table 'shows that the compatibility of the compounds of the invention is very substantially improved compared with that of Compounds A and B.

EXAMPLE 21

Weather resistance 100 parts of polystyrene pellets (sold under the trade name Styron 666 by Asahi Dow Co. Ltd.) were kneaded for 5 minutes at 200° C. in a Brabender plastics kneader with 0.25 part of a stabilizer, to give a homogeneous mixture. The resulting mixture was immediately pressed to form plates of thickness 2-3 mm in a laboratory press. These plates were then pressed for 2 minutes at 180° C. to give plates of thickness 1.5 mm. These were then exposed to light in a Xenon Weather-O-meter (type 65 WR, produced by Atlas Co.) for 600 hours at a black panel temperature of 63±3° C. The yellowness index ($YI_{600}$) of the exposed plates was measured by the method of ASTM-D-1925 and the results are shown in Table 4.

TABLE 4

| Compound No. | $YI_{600}$ |
|---|---|
| 7 | 6.6 |
| 8 | 6.9 |
| 14 | 7.3 |
| 32 | 6.9 |
| Compound A | 8.1 |
| Compound B | 8.7 |
| No addition | 13.3 |

EXAMPLE 22

Weather resistance 100 parts of a thermoplastic polyurethane (sold under the trade name Parapllen Pellet 22S, by Nippon Polyurethane Industry Co. Ltd.) and 0.25 part of a stabilizer were dissolved homogeneously in 300 parts of dimethylformamide. The resulting solution was then drawn off onto a glass plate for form a layer of thickness about 0.4 mm, which was then dried for 20 minutes at 60° C. and then for 15 minutes at 120° C. to give a film of thickness 0.1 mm.

The resulting films were then exposed to light in a Sunshine carbon-arc weather-meter at a black panel temperature of 63±3° C., without water spray. The tensile strength of the exposed films was tested at regular intervals and the time required for the specimens to lose 50% of the original elongation was determined and is reported in hours as the "failure time" in Table 5.

The yellowness index of the films after exposure for 300 hours ($YI_{300}$) was also measured according to the method of ASTM-D-1925.

Part of the film was exposed to nitrogen oxide gas at a concentration of 650 ppm for 2 hours, according to the method of JIS-L-0855. The yellowness index (YI) of the exposed film was then measured by the method of JIS-K-7103. The results are reported in Table 5.

TABLE 5

| Compound No. | Failure time (hours) | $YI_{300}$ | YI |
|---|---|---|---|
| 7 | 780 | 23.2 | 4.4 |
| 8 | 820 | 22.1 | 3.5 |
| 9 | 750 | 24.3 | 3.9 |
| 14 | 760 | 21.0 | 5.2 |
| 32 | 800 | 24.9 | 3.8 |
| Compound A | 580 | 28.5 | 5.4 |
| Compound B | 550 | 27.3 | 5.8 |
| No addition | 250 | 46.3 | 9.2 |

We claim:
1. Compounds of formula (I):

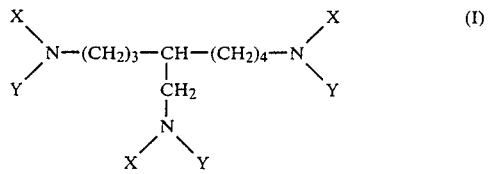

[in which:
the groups represented by X are the same and have the formula (II):

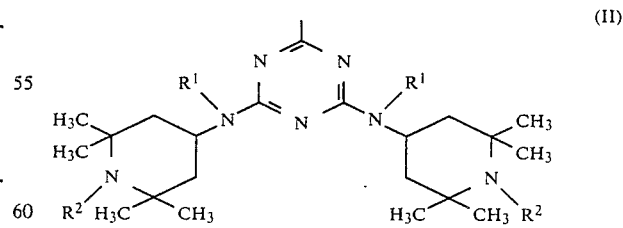

(in which:
$R^1$ represents hydrogen, a $C_1$–$C_{18}$ alkyl group, a $C_2$–$C_{22}$ alkoxyalkyl group, a $C_1$–$C_{18}$ acyl group, an aralkyl group optionally having at least one $C_1$–$C_4$ alkyl or halogen substituent or a group of formula (III):

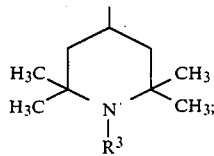

and

R$^2$ and R$^3$ are the same or different and each represents hydrogen, a C$_1$–C$_{18}$ alkyl group, a C$_1$–C$_{18}$ acyl group or an aralkyl group optionally having at least one C$_1$–C$_4$ alkyl or halogen substituent); and Y represents hydrogen, a C$_1$–C$_{18}$ alkyl group, a C$_1$–C$_{18}$ acyl group, an aralkyl group optionally having at least one C$_1$–C$_4$ alkyl or halogen substituent or a group of formula (IV):

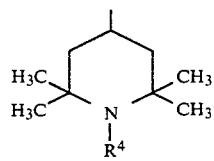

in which R$^4$ has any of the meanings defined for R$^2$]; and acid addition salts thereof.

2. Compounds as claimed in claim 1, in which:
where R$^1$ and Y both represent acyl groups, these acyl groups are the same;
where one of R$^1$ and Y represents an acyl group, the other does not represent hydrogen;
where two or three of R$^2$, R$^3$ and R$^4$ represent acyl groups, these acyl groups are the same; and
where one or two of R$^2$, R$^3$ and R$^4$ represent acyl groups, the other or others do not represent hydrogen atoms.

3. Compounds as claimed in claim 2, in which: where two or more of R$^1$, R$^2$, R$^3$, R$^4$ and Y represent acyl groups, these acyl groups are the same; and
where one or more of R$^1$, R$^2$, R$^3$, R$^4$ and Y represent acyl groups, the other or others do not represent hydrogen atoms.

4. Compounds as claimed in claim 1 or claim 2, in which:
R$^1$ represents hydrogen, C$_1$–C$_{18}$ alkyl, C$_3$–C$_{22}$ alkoxyalkyl, C$_2$–C$_{18}$ acyl, said optionally substituted aralkyl or said group of formula (III);
R$^2$, R$^3$ and R$^4$ represent hydrogen, C$_1$–C$_{18}$ alkyl, C$_2$–C$_{18}$ acyl or said optionally substituted aralkyl; and
Y represents hydrogen, C$_1$–C$_{18}$ alkyl, C$_2$–C$_{18}$ acyl, said optionally substituted aralkyl or said group of formula (IV).

5. Compounds as claimed in claim 1, in which Y represents hydrogen, a C$_1$–C$_{18}$ alkyl group, a C$_2$–C$_{18}$ acyl group or an aralkyl group optionally having a C$_1$–C$_4$ alkyl or halogen substituent.

6. Compounds as claimed in claim 1, in which Y represents hydrogen, methyl or acetyl.

7. Compounds as claimed in claim 1, in which R$^2$ and R$^3$ are the same and each represents hydrogen, methyl or acetyl.

8. Compounds as claimed in claim 2, in which Y, R$^2$ and R$^3$ are the same and each represents hydrogen, methyl or acetyl.

9. Compounds as claimed in claim 1, in which Y and R$^2$, which may be the same or different, each represents hydrogen or methyl, and R$^1$ represents hydrogen, a C$_1$–C$_{18}$ alkyl group or a C$_3$–C$_{22}$ alkoxyalkyl group.

10. Compounds as claimed in claim 1, in which Y and R$^2$, which may be the same or different, each represents hydrogen or methyl, and R$^1$ represents hydrogen or a C$_4$–C$_8$ alkyl group.

11. Compounds as claimed in claim 1, selected from the group consisting of:
1,8-Bis[N-(2,4-bis[N-butyl-N-(2,2,6,6-tetramethylpiperid-4-yl)amino]-1,3,5-triazin-6-yl)amino]-4-[N-(2,4-bis[N-butyl-N-(2,2,6,6-tetramethylpiperid-4-yl)amino]-1,3,5-triazin-6-yl)aminomethyl]octane
1,8-Bis[N-methyl-N-(2,4-bis[N-butyl-N-(1,2,2,6,6-pentamethylpiperid-4-yl)amino]-1,3,5-triazin-6-yl)amino]-4-[N-methyl-N-(2,4-bis[N-butyl-N-(1,2,2,6,6-pentamethylpiperid-4-yl)amino]-1,3,5-triazin-6-yl)aminomethyl]octane
1,8-Bis[N-(2,4-bis[N-octyl-N-(2,2,6,6-tetramethylpiperid-4-yl)amino]-1,3,5-triazin-6-yl)amino]-4-[N-(2,4-bis[N-octyl-N-(2,2,6,6-tetramethylpiperid-4-yl)amino]-1,3,5-triazin-6-yl)aminomethyl]octane
and acid addition salts thereof.

12. 1,8-Bis[N-(2,4-bis[N-butyl-N-(2,2,6,6-tetramethylpiperid-4-yl)amino]-1,3,5-triazin-6-yl)amino]-4-[N-(2,4-bis[N-butyl-N-(2,2,6,6-tetramethylpiperid-4-yl)amino]-1,3,5-triazin-6-yl)aminomethyl]octane and acid addition salts thereof.

13. A synthetic polymer composition comprising a synthetic polymer stabilized against the effects of light by the incorporation of a polymer stabilizer, wherein the stabilizer comprises at least one compound selected from compounds of formula (I):

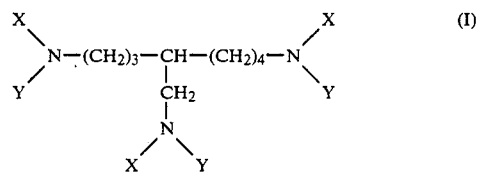

[in which:
the groups represented by X are the same and have the formula (II):

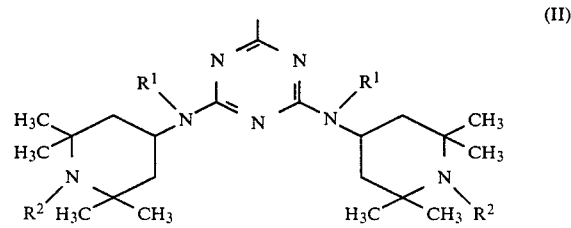

(in which:
R$^1$ represents hydrogen, a C$_1$–C$_{18}$ alkyl group, a C$_2$–C$_{22}$ alkoxyalkyl group, a C$_1$–C$_{18}$ acyl group, an aralkyl group optionally having at least one C$_1$–C$_4$ alkyl or halogen substituent or a group of formula (III):

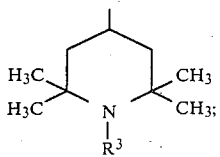

(III)

and

R$^2$ and R$^3$ are the same or different and each represents hydrogen, a C$_1$–C$_{18}$ alkyl group, a C$_1$–C$_{18}$ acyl group or an aralkyl group optionally having at least one C$_1$–C$_4$ alkyl or halogen substituent); and Y represents hydrogen, a C$_1$–C$_{18}$ alkyl group, a C$_1$–C$_{18}$ acyl group, an aralkyl group optionally having at least one C$_1$–C$_4$ alkyl or halogen substituent or a group of formula (IV):

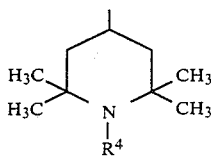

(IV)

in which R$^4$ has any of the meanings defined for R$^2$]; and acid addition salts thereof.

14. A composition as claimed in claim 13, in which:
where R$^1$ and Y both represent acyl groups, these acyl groups are the same;
where one of R$^1$ and Y represents an acyl group, the other does not represent hydrogen;
where two or three of R$^2$, R$^3$ and R$^4$ represent acyl groups, these acyl groups are the same; and
where one or two of R$^2$, R$^3$ and R$^4$ represent acyl groups, the other or others do not represent hydrogen atoms.

15. A composition as claimed in claim 14, in which:
where two or more of R$^1$, R$^2$, R$^3$, R$^4$ and Y represent acyl groups, these acyl groups are the same; and
where one or more of R$^1$, R$^2$, R$^3$, R$^4$ and Y represent acyl groups, the other or others do not represent hydrogen atoms.

16. A composition as claimed in claim 13 or claim 14, in which:
R$^1$ represents hydrogen, C$_1$–C$_{18}$ alkyl, C$_3$–C$_{22}$ alkoxyalkyl, C$_2$–C$_{18}$ acyl, said optionally substituted aralkyl or said group of formula (III);
R$^2$, R$^3$ and R$^4$ represent hydrogen, C$_1$–C$_{18}$ alkyl, C$_2$–C$_{18}$ acyl or said optionally substituted aralkyl; and
Y represents hydrogen, C$_1$–C$_{18}$ alkyl, C$_2$–C$_{18}$ acyl, said optionally substituted aralkyl or said group of formula (IV).

17. A composition as claimed in claim 13, in which Y represents hydrogen, a C$_1$–C$_{18}$ alkyl group, a C$_2$–C$_{18}$ acyl group or an aralkyl group optionally having a C$_1$–C$_4$ alkyl or halogen substituent.

18. A composition as claimed in claim 13, in which Y represents hydrogen, methyl or acetyl.

19. A composition as claimed in claim 13, in which R$^2$ and R$^3$ are the same and each represents hydrogen, methyl or acetyl.

20. A composition as claimed in claim 14, in which Y, R$^2$ and R$^3$ are the same and each represents hydrogen, methyl or acetyl.

21. A composition as claimed in claim 13, in which Y and R$^2$, which may be the same or different, each represents hydrogen or methyl, and R$^1$ represents hydrogen, a C$_1$–C$_{18}$ alkyl group or a C$_3$–C$_{22}$ alkoxyalkyl group.

22. A composition as claimed in claim 13, in which Y and R$^2$, which may be the same or different, each represents hydrogen or methyl, and R$^1$ represents hydrogen or a C$_4$–C$_8$ alkyl group.

23. A composition as claimed in claim 13, wherein said compound is selected from the group consisting of:
1,8-Bis[N-(2,4-bis[N-butyl-N-(2,2,6,6-tetramethylpiperid-4-yl)amino]-1,3,5-triazin-6-yl)amino]-4-[N-(2,4-bis[N-butyl-N-(2,2,6,6-tetramethylpiperid-4-yl)amino]-1,3,5-triazin-6-yl)aminomethyl]octane 1,8-Bis[N-methyl-N-(2,4-bis[N-butyl-N-(1,2,2,6,6-pentamethylpiperid-4-yl)amino]1,3,5-triazin-6-yl)amino]-4-[N-methyl-N-(2,4-bis[N-butyl-N-(1,2,2,6,6-pentamethylpiperid-4-yl)amino]-1,3,5-triazin-6-yl)aminomethyl]octane 1,8-Bis[N-(2,4-bis[N-octyl-N-(2,2,6,6-tetramethylpiperid-4-yl)amino]-1,3,5-triazin-6-yl)amino]-4-[N-(2,4-bis[N-octyl-N-(2,2,6,6-tetramethylpiperid-4-yl)amino]-1,3,5-triazin-6-yl)aminomethyl]octane and acid addition salts thereof.

24. A composition as claimed in claim 13, wherein said compound is selected from 1,8-bis[N-(2,4-bis[N--butyl-N-(2,2,6,6-tetramethylpiperid-4-yl)amino]-1,3,5-triazin-6-yl)amino]-4-[N-(2,4-bis[N-butyl-N-(2,2,6,6-tetramethylpiperid-4-yl)amino]-1,3,5-triazin-6-yl)aminomethyl]octane and acid addition salts thereof.

25. A composition as claimed in claim 13, wherein said stabilizer is present in an amount of from 0.01 to 5% by weight of the polymer.

26. A composition as claimed in claim 13 or claim 24, wherein said polymer is selected from olefin, diene and styrene polymers and said stabilizer is present in an amount of from 0.01 to 2.0% by weight of the polymer.

27. A composition as claimed in claim 13 or claim 24, wherein said polymer is selected from vinyl chloride and vinylidene chloride polymers and said stabilizer is present in an amount of from 0.01 to 1.0% by weight of the polymer.

28. A composition as claimed in claim 13 or claim 24, wherein said polymer is selected from polyurethanes and polyamides and said stabilizer is present in an amount of from 0.01 to 5.0% by weight of the polymer.

* * * * *